United States Patent
Liu et al.

(10) Patent No.: US 11,813,588 B2
(45) Date of Patent: Nov. 14, 2023

(54) CHROMATOGRAPHIC MATERIAL HAVING IMPROVED PH STABILITY, METHOD FOR PREPARATION THEREOF AND USES THEREOF

(71) Applicant: DIONEX CORPORATION, Sunnyvale, CA (US)

(72) Inventors: Xiaodong Liu, Cupertino, CA (US); Xiao Cui, Sunnyvale, CA (US); Xuefei Sun, San Jose, CA (US)

(73) Assignee: Dionex Corporation, Sunnyvale, CA (US)

( * ) Notice: Subject to any disclaimer, the term of this patent is extended or adjusted under 35 U.S.C. 154(b) by 110 days.

(21) Appl. No.: 17/146,447

(22) Filed: Jan. 11, 2021

(65) Prior Publication Data
US 2021/0213420 A1 Jul. 15, 2021

Related U.S. Application Data

(62) Division of application No. 15/543,809, filed as application No. PCT/US2016/012998 on Jan. 12, 2016, now abandoned.
(Continued)

(51) Int. Cl.
*B01D 15/20* (2006.01)
*B01D 15/32* (2006.01)
(Continued)

(52) U.S. Cl.
CPC ............ *B01J 20/287* (2013.01); *B01D 15/20* (2013.01); *B01D 15/325* (2013.01);
(Continued)

(58) Field of Classification Search
CPC ...... B01J 20/262; B01J 20/285; B01J 20/287; B01J 20/289; B01J 20/3078;
(Continued)

(56) References Cited

U.S. PATENT DOCUMENTS

| | | |
|---|---|---|
| 4,746,572 A | 5/1988 | Glajch et al. |
| 5,447,617 A | 9/1995 | Shieh et al. |
| | (Continued) | |

FOREIGN PATENT DOCUMENTS

| | | |
|---|---|---|
| CN | 102215953 A | 10/2011 |
| CN | 102939140 A | 2/2013 |
| | (Continued) | |

OTHER PUBLICATIONS

Isoherranen, N., and S. Soback, "Chromatographic methods for analysis of aminoglycoside antibiotics", Journal of AOAC International, vol. 82, No. 5, pp. 1017-1045. (Year: 1999).*
(Continued)

*Primary Examiner* — Benjamin L Lebron

(57) ABSTRACT

A chromatographic material including a substrate having a surface and having a polymeric layer covalently bound to the surface; the polymeric layer comprising polymer molecules covalently attached to the surface of the substrate, each polymer molecule being attached to the surface via multiple siloxane bonds and each polymer molecule being connected to one or more functionalizing compounds that each comprise a functional group, wherein the polymeric layer is formed by covalently attaching polymer molecules to the surface of the substrate via multiple siloxane bonds, each polymer molecule containing multiple first reactive groups, and reacting the first reactive groups of the attached polymer molecules with at least one functionalizing compound that comprises a second reactive group that is reactive with the first reactive groups and that further comprises a functional group. Preferred conditions of reacting the polymer with the substrate include elevated temperature and reduced pressure.

13 Claims, 11 Drawing Sheets

Scheme 1

Related U.S. Application Data

(60) Provisional application No. 62/103,869, filed on Jan. 15, 2015.

(51) Int. Cl.

| | | |
|---|---|---|
| *B01J 20/289* | (2006.01) | |
| *B01J 20/32* | (2006.01) | |
| *C07H 15/23* | (2006.01) | |
| *C07H 15/232* | (2006.01) | |
| *C07H 15/234* | (2006.01) | |
| *C07H 15/238* | (2006.01) | |
| *B01J 20/287* | (2006.01) | |
| *B01J 20/30* | (2006.01) | |
| *C07D 493/04* | (2006.01) | |
| *C07H 1/06* | (2006.01) | |
| *C07H 15/224* | (2006.01) | |
| *C08G 77/392* | (2006.01) | |

(52) U.S. Cl.
CPC ......... *B01J 20/289* (2013.01); *B01J 20/3078* (2013.01); *B01J 20/3092* (2013.01); *B01J 20/3204* (2013.01); *B01J 20/328* (2013.01); *B01J 20/3217* (2013.01); *B01J 20/3272* (2013.01); *C07D 493/04* (2013.01); *C07H 1/06* (2013.01); *C07H 15/224* (2013.01); *C07H 15/23* (2013.01); *C07H 15/232* (2013.01); *C07H 15/234* (2013.01); *C07H 15/238* (2013.01); *C08G 77/392* (2013.01); *B01J 2220/44* (2013.01); *B01J 2220/52* (2013.01); *B01J 2220/54* (2013.01); *B01J 2220/58* (2013.01)

(58) Field of Classification Search
CPC ............... B01J 20/3092; B01J 20/3204; B01J 20/3217; B01J 20/3272; B01J 20/328; B01J 2220/44; B01J 2220/42; B01J 2220/54; B01J 2220/58; B01J 2220/86; B01D 15/20; B01D 15/325; C07D 493/04; C07H 1/06; C07H 15/224; C07H 15/23; C07H 15/232; C07H 15/234; C07H 15/238; C08G 77/20; C08G 77/70; C08G 77/392; G01N 27/44752; G01N 27/44747; C08L 3/04; C09D 183/04; C09J 183/04

See application file for complete search history.

(56) References Cited

U.S. PATENT DOCUMENTS

| | | |
|---|---|---|
| 5,840,388 A | 11/1998 | Karger et al. |
| 9,144,756 B2 | 9/2015 | Liu et al. |
| 10,900,938 B2 | 1/2021 | Iovanni et al. |
| 2003/0219597 A1 | 11/2003 | Carr et al. |
| 2004/0170843 A1 | 9/2004 | Moritani et al. |
| 2008/0193651 A1 | 8/2008 | Lubda et al. |
| 2011/0220575 A1 | 9/2011 | Deorkar et al. |
| 2012/0029154 A1 | 2/2012 | Deetz et al. |
| 2014/0243512 A1 | 8/2014 | Arendt et al. |
| 2014/0309447 A1 | 10/2014 | Standke et al. |
| 2021/0181222 A1 | 6/2021 | Otomo |

FOREIGN PATENT DOCUMENTS

| | | |
|---|---|---|
| CN | 209372766 U | 9/2019 |
| GB | 1456865 A | 12/1976 |
| JP | H05279411 A | 10/1993 |
| JP | H08508577 A | 9/1996 |
| JP | H10502175 A | 2/1998 |
| JP | 2007523331 A | 8/2007 |
| JP | 2012032392 A | 2/2012 |
| JP | 2013067796 A | 4/2013 |
| JP | 2014527907 A | 10/2014 |
| JP | 2019197016 A | 5/2018 |
| KR | 101218184 B1 | 9/2011 |
| WO | 9520157 A1 | 7/1995 |

OTHER PUBLICATIONS

Neue, U., et al., "Differences in preparatie loadability between the charged and uncharged forms of ionizable compounds", Journal of Chromatography A, 1030, pp. 123-134. (Year: 2004).*

Umezawa, H., and S. Kondo, "Ion-exchange chromatography of aminoglycoside antibiotics", Methods in Enzymology, 43, pp. 263-278. (Year: 1975).*

"Multifunctional Autosampler Dramatically Improves GC/MS Analysis Productivity" Shimadzu, Jun. 2020.

"Thermo Scientific TriPlus RSH Autosampler Integrated Sampling System" Thermo Fisher Brochure, 2011.

* cited by examiner

Scheme 1

Scheme 2

Scheme 3

Scheme 4

Phases 35 - 38

Scheme 5

Phases 19 - 22 → Phases 41 - 46

Scheme 6

Phase 22          Phase 47

Scheme 7

CHROMATOGRAPHIC MATERIAL HAVING IMPROVED PH STABILITY, METHOD FOR PREPARATION THEREOF AND USES THEREOF

CROSS REFERENCE TO RELATED APPLICATIONS

The present application is a divisional and claims the priority benefit of co-pending U.S. patent application Ser. No. 15/543,809, filed Jul. 14, 2017, which is the United States National Stage Application, under 35 U.S.C. § 371, of International Application PCT/US2016/012998, filed Jan. 12, 2016, entitled "CHROMATOGRAPHIC MATERIAL HAVING IMPROVED pH STABILITY, METHOD FOR PREPARATION THEREOF AND USES THEREOF," which claims the priority benefit to U.S. Provisional Patent Application Ser. No. 62/103,869 by Xiaodong LIU, Xiao CUI, Xuefei SUN for "CHROMATOGRAPHIC MATERIAL HAVING IMPROVED pH STABILITY, METHOD FOR PREPARATION THEREOF AND USES THEREOF" filed Jan. 15, 2015, the entire disclosure of which is incorporated by reference.

FIELD OF THE INVENTION

This invention relates to the field of chromatographic sample separation that includes liquid chromatography and solid phase extraction and, in particular, it relates to material and the synthesis of material for use as a stationary phase in chromatographic sample separation. The invention further relates to uses of the material, in particular in the separation of aminoglycoside antibiotics. The invention also relates to chromatographic columns and solid phase extraction columns containing the material as a stationary phase.

BACKGROUND

Liquid chromatography (LC), e.g. HPLC and UHPLC, and solid phase extraction (SPE) are used routinely in both analytical and preparative chromatography applications for determination of the quality and quantity of analytes in a variety of samples. In these chromatographic techniques, separation of a sample comprising a mixture of components (also termed analytes) is achieved by conveying the sample in a liquid mobile phase through a stationary phase in a column, thereby causing the sample to separate into its components due to different partitioning between the mobile and stationary phases of each of the components (i.e. the components have different partition coefficients). The stationary phase is typically in the form of a bed of particles packed within the column, or in the form of a monolithic material held in the column.

A bed of non-porous particles has a relatively low sample capacity. Therefore, porous particles are commonly used which contain a network of pores to increase the surface area of the stationary phase and thus improve the capacity of the separation. The porous particles may be fully porous, wherein the pores extend throughout the bulk of the particles. As an alternative to fully porous particles, more recently use has been made of so-called fused core particles, which are also termed superficially porous particles. These are particles that have a non-porous core (also termed a fused or solid core) and are porous only in an outer layer or region that surrounds the non-porous core.

The selectivity of a stationary phase for analytes is mainly governed by the column chemistry, which is key in LC separation. The column chemistry is routinely controlled by modifying the surface of the stationary phase, commonly by bonding ligands to the surface.

Silica particles are commonly used as the stationary phase, either as non-porous, fully porous or superficially porous particles. Silica based HPLC columns are used for a broad range of applications because of their excellent physical strength, high efficiency and mature surface bonding chemistry.

However, silica based columns have pH limitations. Under acidic conditions, the bonded ligands can be cleaved at the siloxane (Si—O—Si) linkage between the silica surface and the ligand, resulting in loss of hydrophobic retention in the case of a C18 bonded column. Under alkaline conditions, the hydroxide ions can erode the silica substrate by destroying the siloxane linkages in the silica backbone, causing the collapse of the packed bed or headspace (void) in the column.

Stationary phase media for HPLC separations are commonly produced by modifying a silica surface with silylating agents. Monofunctional silylating agents are often used to form monolayer surface coatings, while di- and tri-functional silylating agents are used to form polymeric coatings on silica surfaces generally resulting in improved chemical stability. However, the use of some silylating agents results in coatings with undesirable properties including instability to hydrolysis and inadequate masking of acidic silanols on silica surfaces. Consequently, the typical working pH range for C18 silica columns prepared from these approaches is 2-8.

Several attempts have been made to make pH stable silica stationary phases for HPLC applications.

In one approach to make stable separation media for HPLC applications, Fisk et al (WO 00/45951) discloses a process to prepare porous inorganic/organic hybrid silica particles as a solid support for further surface modifications. After reacting with silylating agents, such as dimethyl octadecyl chlorosilane, the resulting materials showed decreased silanol activity and enhanced hydrolytic stability with an extended operating pH range of 1 to 13. The disadvantages of this approach can be considered to lie in lower capacity and inferior column efficiency, which is mainly due to fewer available surface silanols and somewhat polymeric nature of this material.

In another approach, Glajch et al. (U.S. Pat. No. 4,705, 725) describes separation medias modified by covalently bonding a mono-functional silane to the surface the silane containing two sterically hindering groups and an additional functional group attached to the silicon atom. The columns packed with such materials showed enhanced hydrolytic stability at low pH. However, the use of such silylating agents is disadvantageous because bonded phases often have lower surface coverage, resulting in decreased phase stability under high pH conditions.

In another method, J. J. Kirkland et al. reports the preparation of bidentate silane stationary phases for reversed-phase HPLC (J. J. Kirkland; J. B. Adams, Jr.; M. A. van Straten; H. A. Claessens, Analytic Chemistry, 70: 4344-4352 (1998)). Such stationary phases display good hydrolytic stability at low, middle, and high pHs (1.5-11.5) and satisfactory column efficiency. Similarly, Liu et al (U.S. Pat. No. 7,074,491) describes polar-embedded bidentate reversed-phase materials that exhibit an extended pH range (pH 1.5-10.5) and unique selectivity.

M. J. Wirth describes immobilizing a monolayer of silane ligands on a silica surface using horizontal polymerization of mixed trifunctional silanes, which exhibit superior hydrolytic stability compared to the conventional monomeric stationary phase (M. J. Wirth, H. O. Fatunmbi, Anal. Chem. 65 (1993) 822). The obtained silica stationary phase is reported to be stable over 100 hours exposure to pH 1.8 solution (50° C.) and degrades less than 5% after 30-h treatment of pH 10 solution. Whilst the horizontal polymer layer assists in protecting the silica surface from attacking, the siloxane linkage generated in the polymer chain is still exposed to the environment and will be hydrolyzed easily under extreme conditions, which will impair the long-term stability of the silica phase.

The use of polymer encapsulated silica is another approach to improve stationary phase stability by combining the high mechanical strength of a silica substrate and the high chemical stability of polymers. The polymer layer is formed on the silica surface to protect it from aggressive pH conditions. Several hydrophobic polymers, such as polymethyloctadecylsiloxane (M. J. J. Hetero, J. W. De Haan, H. A. Claessens, C. A. Cramers, A. Deege, G. Schomburg, J. Chromatogr. A 540 (1991) 53) and polybutadiene (M. Hanson, K. K. Unger, G. Schomburg, J. Chromatogr. A 517 (1990) 269), have been applied to encapsulate silica particles. These coating layers are first physically deposited on the silica surface, and then cross-linked or chemically bonded to the substrate. However, several disadvantages have been reported such as non-uniform surface coverage and less than desired pH stability at pH extremes. In addition, stationary phases prepared by this approach have inherent issues of column bleeding and manufacturing reproducibility. The polymer layer can also be attached onto inorganic support surface at multiple-points. For example, the silica surface can be modified with a copolymer of styrene and vinylmethyldiethoxysilane by refluxing the toluene suspension for 5 hours (A. Kurganov, V. Davankov, T. Isajeva, K. Unger, F. Eisenbeiss, J. Chromatogr. A 660 (1994) 97). However, the obtained polymer layer is not sufficiently stable because the immobilization efficiency is low due to the steric hindrance of the copolymer chain. The immobilized polymer layer has to be cross-linked to improve its hydrolytic stability under the aggressive environment.

H. Engelhardt et al. have described improved silica stationary phase stability by the copolymerization of vinyl modified silica with acrylic acid derivatives. In the first step the silica is modified with a silane containing an individual vinyl group in the presence of triethylamine. In the second step, the surface is covered by polymerizing an acrylic acid derivative containing the desired functionality with the immobilized vinyl groups in solution using α,α'-azoisobutyronitrile (AIBN) as the initiator. The free radical polymerization was carried out at temperature of between 80° C. and 120° C. for 2-3 hours. The obtained polymer encapsulated silica phases had longer life time than the conventional brush type phase under basic conditions. However, they were not adequately stable and failed quickly when using at pH higher than 9.0 (H. Engelhardt, H. Löw, W. Eberhardt, M. Maß, Chromatographia, 27 (1989) 535).

An important application of pH-stable stationary phases is the simultaneous qualitative and quantitative determination of aminoglycosides by HPLC. Aminoglycoside antibiotics are frequently used as clinical and veterinary medicines to treat infections caused by gram-negative bacteria. However, these antibiotics can cause varying degree of ototoxicity and nephrotoxicity. Therefore, it is very important to develop sensitive and reliable analytical methods to determine aminoglycoside content in drug preparation and monitor aminoglycoside residues in different sample matrices. However, HPLC separations of aminoglycosides are difficult to achieve because of structural similarity of aminoglycosides, very high hydrophilicity, and lack of chromophores. Ion-pairing reversed-phase liquid chromatography (IP-RPLC), ion chromatography (IC), and hydrophilic interaction liquid chromatography (HILIC) are employed to analyze aminoglycosides without any derivations. Reversed-phase columns (e.g. C18) are the column of choice when it comes to aminoglycoside antibiotics because they exhibit desired selectivity, high efficiency and excellent mechanical stability. However, the requirement for extremely acidic conditions (e.g. pH⁻1) makes most silica-based C18 unsuitable for this application. Most C18 columns last merely 24 to 48 hours before losing more than 20% of their reverse phase capacity.

SUMMARY

According to an aspect of the invention there is provided:
a chromatographic material comprising:
a substrate having a surface and having a polymeric layer covalently bound to the surface;
the polymeric layer comprising polymer molecules covalently attached to the surface of the substrate, each polymer molecule being attached to the surface via multiple siloxane bonds (i.e. Si—O—Si bonds) and each polymer molecule being connected to one or more (preferably multiple) functionalizing compounds that each comprise a functional group. The functional group in particular desirably has a chromatographic functionality. In particular, the functional group is alkyl or aryl, preferably C4-C30 alkyl or aryl.

The material can therefore be seen as a polymer encapsulated material.

The polymer preferably comprises a siloxane polymer or a polymer containing silyl groups. The silyl groups of such polymer allow the polymer to attach to a silica substrate via siloxane bonds.

The polymeric layer is preferably formed by covalently attaching at least one polymer molecule to the surface of the substrate, each polymer molecule being attached to the surface via multiple siloxane bonds and each polymer molecule containing multiple first reactive groups (in particular olefinic groups, especially vinyl groups or allyl groups, or thiol groups), and reacting the first reactive groups of the attached polymer molecules with at least one functionalizing compound that comprises a second reactive group that is reactive with the first reactive groups (in particular an olefinic group, or —SH (thiol) group) and that further comprises a functional group, in particular having chromatographic functionality, in particular alkyl or aryl, preferably C4-C30 alkyl or aryl.

In a particularly preferred embodiment, the invention provides:
a chromatographic material comprising:
a silica substrate having a surface and having a polymeric layer covalently bound to the surface;
the polymeric layer being formed by covalently attaching at least one polymer to the surface of the substrate the polymer being selected from a vinylalkoxysiloxane polymer and a vinyl-functional silyl-modified polybutadiene, each polymer molecule being attached to the surface via multiple siloxane bonds (Si—O—Si) and each polymer molecule containing multiple vinyl groups, and reacting the vinyl groups of the attached polymer molecules with at least one functionalizing compound that comprises a second reactive group reactive with the vinyl groups of the attached polymer molecules, the second reactive group being selected from a vinyl, allyl, or thiol group, and that further comprises a C14-C22 alkyl functional group (preferably C18 alkyl), in particular the functional group having chromatographic functionality such as reverse phase chromatographic functionality.

The material according to the invention thus comprises a substrate, a polymeric layer bound to the substrate and a functional compound bound to the polymeric layer. The polymeric layer thereby acts to connect the functional compound to the substrate and protects the substrate from hydrolysis. The functional compound allows chromatographic separation of analytes, e.g. by reverse phase separation.

According to another aspect of the invention there is provided a method of forming functionalized silica for chromatographic use, the method comprising:

in a first stage, reacting silica with at least one first functionalizing compound under conditions of elevated temperature and reduced pressure;

the first functionalizing compound or compounds comprising one or more silyl groups for reacting with the surface of the silica and one or more first reactive groups, thereby covalently attaching the first functionalizing compound or compounds to the surface of the silica and leaving the first reactive groups unreacted; and in a second stage, reacting the one or more first reactive groups of the surface bound first functionalizing compound or compounds with at least one second functionalizing compound that comprises one or more second reactive groups reactive with the one or more first reactive groups and that further comprises a functional group.

According to still another aspect of the invention there is provided a method of forming functionalized silica for chromatographic use, the method comprising:

in a first stage, reacting silica with at least one first functionalizing compound under conditions of elevated temperature;

the first functionalizing compound or compounds comprising a polymer or polymers having multiple silyl groups for reacting with the surface of the silica and multiple first reactive groups, thereby covalently attaching the first functionalizing compound or compounds to the surface of the silica and leaving the first reactive groups unreacted; and in a second stage, reacting the one or more first reactive groups of the surface bound first functionalizing compound or compounds with at least one second functionalizing compound that comprises one or more second reactive groups reactive with the one or more first reactive groups and that further comprises a functional group.

Thus, the invention relates to the preparation of stationary phase material by functionalizing silica substrates using polymers under elevated reaction temperature and preferably reduced pressures. The material has been found to be very pH stable and useful as separation media.

In the process using elevated reaction temperature and reduced pressure, the at least one first functionalizing compound is preferably a polymer as hereafter described, i.e. the polymer for covalent attachment to the surface of the substrate, or may be a silane monomer (e.g. a vinylsilane). The polymer in particular may be of the type: siloxane polymer (e.g. vinyl siloxane polymer) or silyl modified polymer such as silyl modified polybutadiene, as hereafter described.

The second functionalizing compound is preferably a hydrocarbon compound comprising an olefinic group or bond, especially an alkyl compound, or is an alkyl thiol or aryl thiol as hereafter described.

The first bonded layer of the polymeric layer on the surface, i.e. formed from the first functionalizing compound or polymer, is preferably prepared from a polymer with certain sizes (molecular weights) that are not too small for good stability and not too large so as to have a tendency to block the pores thereby resulting in poor chromatography. The second bonded (functionalizing) layer of the polymeric layer is preferably formed by co-polymerization of the second functionalizing compound (comprising functional groups (e.g. alkyl or aryl) and olefinic reactive groups (e.g. vinyl, allyl, styrenic, acrylamide, acrylate, etc)) with the first reactive groups in the first bonded layer (e.g. vinyl, allyl groups).

The second stage of the process preferably provides polymer encapsulation of the silica phases using free radical polymerization of the polymeric layer.

The invention utilises a polymer (which term herein includes a molecule that may be termed elsewhere an oligomer) to form a polymeric layer, the polymeric layer having multiple reactive (e.g. vinyl) groups and multiple silyl groups for attaching to a surface which gives better coverage and protection of the surface siloxane bonds than using simple small vinyl-functional silane molecules as described in Engelhardt et al (Chromatographia, 27 (1989) 535). In the latter case, the surface siloxane bonds are left more exposed to attack under acid or alkaline conditions. In tests it has been found that use of a polymer in the manner described herein may provide 50 to 100% higher stability at pH extremes (pH1 and pH 13) compared to use of a corresponding vinylsilane monomeric molecule.

Materials provided by the invention may exhibit exceptional stability under acidic conditions and greatly improved ruggedness under alkaline conditions. A column (such as a chromatography or solid phase extraction column) packed with such material may be suitable for separating aminoglycoside antibiotics with excellent resolution and chemical ruggedness. A C18-functionalized material according to the invention has been found to exhibit excellent hydrolytic stability at extremely low pH conditions and shows greatly improved stability under alkaline conditions. A column packed with such C18-functionalized material has proved to be suitable for separating aminoglycoside antibiotics with extended lifetime and resolution power.

According to a further aspect of the invention there is provided a method of separating aminoglycoside antibiotics comprising flowing a mobile phase containing a sample comprising one or more aminoglycoside antibiotics through a column to chromatographically separate the one or more aminoglycoside antibiotics from each other and/or from one or more other components of the sample, wherein the column is packed with the chromatographic material according to the present invention. Preferably the pH of the mobile phase is about 1 or less, which is typical when separating aminoglycoside antibiotics. The chromatographic material of the invention in other applications may also be useful with alkaline phases, e.g. at about pH 11.

In an embodiment of making the chromatographic material as described above, the method can further include reacting the silica during the first stage and/or second stage with a reduced pressure (in particular below atmospheric pressure and preferably below 500 mbar).

In an embodiment, a chromatographic material can be made by a process where the process includes, in a first stage, reacting silica with at least one first functionalizing compound under conditions of at least about 100° C. and of less than 500 mbar. The first functionalizing compound or compounds includes one or more silyl groups for reacting with the surface of the silica; and one or more first reactive groups. Thereby, the first functionalizing compound or compounds is covalently attached to the surface of the silica and leaves the first reactive groups unreacted. In a second stage, the one or more first reactive groups of the surface bound first functionalizing compound or compounds is reacted with at least one second functionalizing compound. The second functionalizing compound includes one or more second reactive groups reactive with the one or more first reactive groups; and a functional group. Whereby, a retention time of a chromatographic analysis of a hydrophobic neutral compound does not vary by more than +/−10% while a mobile phase is flowed through the chromatographic material for more than 20 hours, where the mobile phase has a pH of about 1 or less. The hydrophobic neutral compound may include acetanilide.

In regards to the chromatographic material described above, it may further include repeating a step of reacting the silica with the at least one first functionalizing compound under conditions of at least about 100° C. and of less than 500 mbar during the first stage, but before the second stage. A step of reacting the one or more first reactive groups of the surface bound first functionalizing compound or compounds with the at least one second functionalizing compound under conditions of at least about 100° C. and of less than 500 mbar during the second stage can be repeated.

In regards to the chromatographic material described above, the reacting of silica with at least one first functionalizing compound in the first stage can be performed in the absence of a solvent. Similarly, the reacting of the one or more first reactive groups of the surface bound first functionalizing compound or compounds with the at least one second functionalizing compound in the second stage can be performed in the absence of a solvent.

In regards to the chromatographic material described above, the reacting of silica with at least one first functionalizing compound in the first stage can be performed in the presence of a catalyst.

In regards to the chromatographic material described above, the first functionalizing compound may include a vinylsiloxane polymer. The vinylsiloxane polymer can have a formula I:

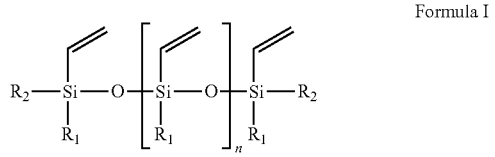

Formula I wherein n is an integer from 3 to 100, $R_1$ and $R_2$ are independently selected from the group consisting of: alkoxy, hydroxyl, and halo.

In regards to the chromatographic material described above, the first reactive group can include a member selected from the group consisting of vinyl groups and allyl groups. The functional group can include a member selected from the group consisting of an alkyl and an aryl. More specifically, the functional group can include a C4-C30 alkyl. The second reactive group can include a member selected from the group consisting of a vinyl group, an allyl group and a thiol group.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

DETAILED DESCRIPTION OF EMBODIMENTS

Figure 1:
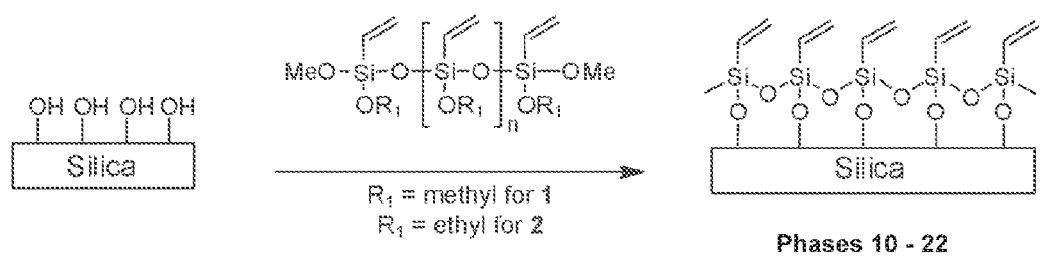
FIG. 1 (Scheme 1) shows a preparation of vinyl functionalized silica using vinyl silane polymer.

Various preferred features, embodiments and examples of the invention will now be described in more detail.

Definitions

Herein the term "hydrocarbon" and the like (e.g. hydrocarbon moiety, hydrocarbyls etc.) includes alkyl and aryl groups as herein defined.

Herein the term "carbon chain length" or "total carbon chain length" means the longest carbon chain length in the molecule. Thus, in the case of straight chains, the chain lengths are numbered simply as, for example:

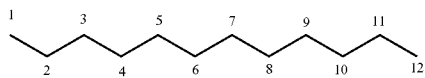

Chain branches are not included in the chain length count, as, for example:

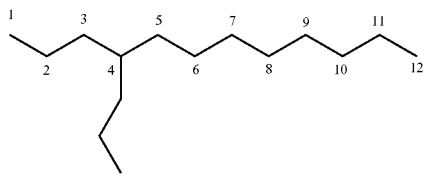

In the case of an aryl group, the number of carbon atoms in the benzene ring counts as 4 in the chain length for a para-linkage and 3 for a meta-linkage, for example:

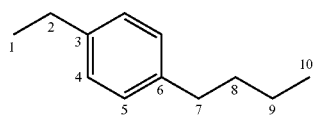

Any heteroatoms are not counted as carbon atoms in the carbon chain length.

Herein the term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl (e.g., —$CH_2$—$CH_2$—$CH_3$, —$CH_2$—$CH_2$—$CH_2$—), isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl". Alkyl groups that are limited to hydrocarbon groups are termed "homoalkyl". The term "alkyl" can also mean "alkylene" or "alkyldiyl" as well as alkylidene in those cases where the alkyl group is a divalent radical.

Typical alkyl groups include, but are not limited to: methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

Herein the term "alkylene" or "alkyldiyl" by itself or as part of another substituent means a divalent radical derived from an alkyl group, as exemplified, but not limited to, by —$CH_2CH_2CH_2$— (propylene or propane-1,3-diyl), and further includes those groups described below as "heteroalkylene". Typically, an alkyl (or alkylene) group will have from 1 to about 30 carbon atoms, preferably from 1 to about 25 carbon atoms, more preferably from 1 to about 20 carbon atoms, even more preferably from 1 to about 15 carbon atoms and most preferably from 1 to about 10 carbon atoms. A "lower alkyl", "lower alkylene" or "lower alkyldiyl" is a shorter chain alkyl, alkylene or alkyldiyl group, generally having about 10 or fewer carbon atoms, about 8 or fewer carbon atoms, about 6 or fewer carbon atoms or about 4 or fewer carbon atoms.

Herein the term "alkylidene" by itself or as part of another substituent means a divalent radical derived from an alkyl group, as exemplified, but not limited, by $CH_3CH_2CH_2$= (propylidene). Typically, an alkylidene group will have from 1 to about 30 carbon atoms, preferably from 1 to about 25 carbon atoms, more preferably from 1 to about 20 carbon atoms, even more preferably from 1 to about 15 carbon atoms and most preferably from 1 to about 10 carbon atoms. A "lower alkyl" or "lower alkylidene" is a shorter chain alkyl or alkylidene group, generally having about 10 or fewer carbon atoms, about 8 or fewer carbon atoms, about 6 or fewer carbon atoms or about 4 or fewer carbon atoms.

Herein the terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

Herein the term "heteroalkyl," by itself or in combination with another term, means, unless otherwise stated, a stable straight or branched chain, or cyclic hydrocarbon radical, or combinations thereof, comprising the stated number of carbon atoms and at least one heteroatom selected from the group consisting of O, N, Si, S and B, and wherein the nitrogen and sulfur atoms may optionally be oxidized and the nitrogen heteroatom may optionally be quaternized. The heteroatom(s) O, N, B, S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—$NHCH_3$, —$CH_2$—$CH_2$—$N(CH_3)$—$CH_3$, —$CH_2$—S—$CH_2$—$CH_3$, —$CH_2$—$CH_2$, —S(O)—$CH_3$, —$CH_2$—$CH_2$—$S(O)_2$—$CH_3$, —CH=CH—O—$CH_3$, —$Si(CH_3)_3$, —$CH_2$—CH=N—$OCH_3$, and —CH=CH—$N(CH_3)$—$CH_3$. Up to two heteroatoms may be consecutive, such as, for example, —$CH_2$—NH—$OCH_3$ and —$CH_2$—O—$Si(CH_3)_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Optionally, for alkylene and heteroalkylene linking groups, no orientation of the linking group is implied by the direction in which the formula of the linking group is written. For example, the formula —$CO_2R'$— optionally represents both —C(O)OR' and —OC(O)R'.

Herein the terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

Herein the terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is meant to include, but not be limited to, trifluoromethyl, 2,2,2-trifluoroethyl, 4-chlorobutyl, 3-bromopropyl, and the like.

Herein the term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, S, Si and B, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, herein the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —OS(O)$_2$R', —S(O)$_2$NR'R", —NRSO$_2$R', —CN and —NO$_2$ in a number ranging from zero to (2m'+1), where m' is the total number of carbon atoms in such radical. R', R", R"' and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are generically referred to as "aryl group substituents". The substituents are selected from, for example: substituted or unsubstituted alkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro ($C_1$-$C_4$)alkyl, in a number ranging from zero to the total number of open valences on the aromatic ring system; and where R', R", R"' and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R"' and R"" groups when more than one of these groups is present.

The substrate may be a particulate or monolithic substrate, preferably particulate. The substrate material may be a metal oxide (which term herein includes a metalloid oxide, such as silica for example, and includes an inorganic-organic hybrid material (especially a metal oxide-organic hybrid material), as described in WO 00/45951 for example). The substrate may, in particular, be silica ($SiO_2$), which term herein includes a silica/organo hybrid, alumina ($Al_2O_3$), titania ($TiO_2$), or zirconia ($ZrO_2$) substrate. A silica (which term herein includes a silica/organo hybrid) substrate is most preferred. The surface of the silica may be terminated by silanol (hydroxyl) groups prior to covalently attaching the polymer, e.g. so that silyl groups of the polymer as herein described react with said surface silanol groups.

The polymeric layer is covalently bound to the surface of the substrate. The polymeric layer is formed by covalently attaching at least one polymer (which term includes oligomers) to the surface of the substrate. Each polymer molecule is attached to the surface via multiple siloxane bonds (Si—O—Si). Each polymer molecule contains multiple reactive groups (in particular olefinic groups, especially vinyl groups or allyl groups, or thiol groups) and these reactive groups of the attached polymer molecules are reacted with the at least one functionalizing compound.

In more detail, the polymeric layer is formed by covalently attaching at least one polymer (which term includes oligomers) to the surface of the substrate, each polymer molecule being attached to the surface via multiple siloxane bonds (Si—O—Si) and each polymer molecule containing multiple first reactive groups (in particular olefinic groups, especially vinyl groups or allyl groups, or thiol groups), and reacting the first reactive groups of the attached polymer molecules with at least one functionalizing compound that comprises a second reactive group (i.e. at least one second reactive group) that is reactive with the first reactive group (in particular wherein the second reactive group comprises an olefinic group (the term olefinic herein including groups having reactive double bonds, e.g. vinyl, allyl, styrenyl, acrylamidyl, acrylate), or thiol group (—SH)) and that further comprises a functional group. The functional group preferably has chromatographic functionality. In particular, the functional group comprises alkyl or aryl, preferably C4-C30 alkyl or aryl.

The polymer molecules are not formed on the surface from surface bound monomers; the polymer molecules are already polymer molecules before they are attached to the surface. In this way, the polymer (having multiple first reactive groups and multiple silyl groups) bonds to the surface of the silica, which gives better coverage and protection of the surface siloxane bonds than using small vinyl-functional silane molecules, as in Engelhardt et al above, that leave the surface siloxane bonds more exposed to attack under acid/alkaline conditions.

The polymer preferably comprises and utilises a silyl group or groups for attaching the polymer to the substrate (especially silica substrate). The silyl group accordingly is preferably an activated silyl group, i.e. having groups (leaving groups) that can react with a substrate (especially silica) surface and enable attachment of the polymer to the substrate surface. The silyl groups in this way covalently bond the polymer to the silica substrate via siloxane bonds (Si—O—Si). A first Si atom in the siloxane bond is derived from the silyl group. A second Si atom in the siloxane bond is derived from the silica, i.e. the silica surface.

The silyl group or groups of the polymer molecules preferably have a formula:

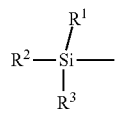

wherein at least one of $R^1$, $R^2$, $R^3$ is a leaving group. Preferably, $R^1$, $R^2$, $R^3$ are independently selected from an oxygen atom (e.g. that connects to a substrate (silicon) atom in the substrate or connects to another silicon atom of the polymer), a hydroxyl group, a halogen atom, an alkoxy group (i.e. methoxy, ethoxy, etc), a dialkylamino group, an acyl group, an alkyl group (optionally a heteroalkyl group or a heterocycloalkyl group), an aryl group (optionally a heteroaryl group), or a reactive group (i.e. the first reactive group described herein, for example an olefinic group, such as vinyl, allyl etc.).

The groups $R^1$, $R^2$ and $R^3$ may be the same or all different. Preferably, at least one, optionally two of $R^1$, $R^2$, $R^3$ groups is a leaving group. More preferably, at least one of $R^1$, $R^2$, $R^3$ groups is an alkoxy group (preferably methoxy, ethoxy or propoxy, especially methoxy), a dialkylamino group, or a halogen atom.

In the case of vinylsiloxane polymers, typically the silyl group has a leaving group (terminal silyl groups may have two leaving groups), a reactive group and two bonds (terminal silyl groups have one such bond) to respective oxygen atoms that are connected to adjacent silicon atoms of the polymer). The leaving groups are capable of allowing the polymer to form the siloxane bonds to the substrate silica surface.

The polymer comprises multiple reactive groups, herein termed first reactive groups. The first reactive groups preferably are reactive olefinic groups or reactive thiol groups, especially olefinic groups. The reactive olefinic groups of the polymer are preferably vinyl or allyl groups. The multiple reactive groups are preferably all of the same type, e.g. all vinyl.

The polymer preferably has a "fixed" distance between adjacent first reactive groups (e.g. between adjacent vinyl groups), i.e. the distance between adjacent first reactive groups is substantially uniform for all the reactive groups in the polymer molecule. For example, homopolymer 1 of FIG. 1 has a repeating 3 atoms interval in between the first reactive groups (e.g., vinyl groups).

The at least one polymer, in one type of embodiment, preferably comprises at least a siloxane polymer having reactive groups. In particular, the at least one polymer, in this type of embodiment, preferably comprises at least vinyl siloxane polymer (i.e. siloxane polymer having reactive vinyl groups). The size (i.e. number average molecular weight, $MW_n$) of the (optionally vinyl) siloxane polymer is preferably 500-10,000 daltons (Da). The vinyl siloxane polymer is preferably a vinylalkoxysiloxane polymer.

The vinyl siloxane polymer may have a formula I in one preferred embodiment:

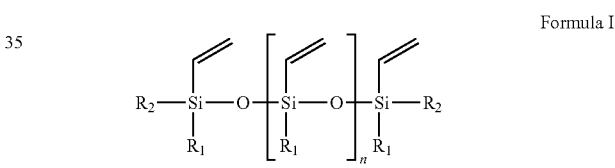

Formula I wherein n is an integer from 3 to 100 $R_1$, and $R_2$ are independently selected from alkoxy, especially methoxy and ethoxy, hydroxyl and halo (especially Cl). $R_1$ and $R_2$ are preferably independently selected from alkoxy, especially methoxy and ethoxy, and hydroxyl. $R_1$ and $R_2$ are more preferably independently selected from alkoxy, especially methoxy and ethoxy. $R_1$ and $R_2$ are especially preferably the same, preferably both either methoxy or ethoxy.

In a preferred embodiment, the vinyl siloxane polymer may have a formula II:

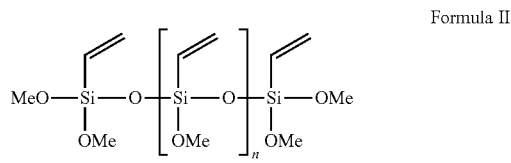

Formula II

Alternatively, a polymer which has ethoxy groups, or hydroxyl groups, in place of the methoxy groups in formula II is also a preferred embodiment.

A surface bound polymeric layer formed from polymer of formula I or II (having methoxy or ethoxy groups) preferably has a general structure as follows, wherein vinyl reactive groups are present:

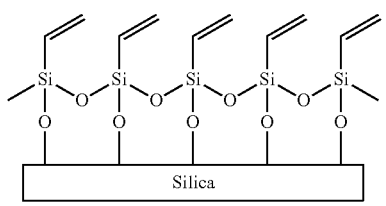 [SMILES: C=C[Si](C)(OC)O[Si](C=C)(OC)O[Si](C=C)(OC)O[Si](C=C)(OC)O[Si](C)(C=C)OC]

In the formula I or II, any number of the vinyl groups may be replaced by alkyl groups, e.g. C1-C4 alkyl, especially C1-C3 alkyl.

The vinyl siloxane polymer may be a co-polymer, e.g. containing a mixture of vinyl siloxane units and alkyl siloxane units (especially C1-C4 alkyl). The co-polymer may have a nominal formula III for example:

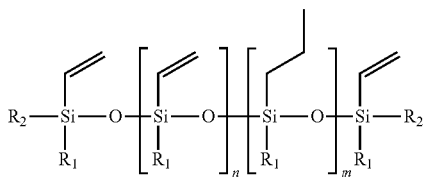

Formula III wherein $R_1$, and $R_2$ are defined as above for formulae I and II and wherein n is an integer from 3 to 100 and m is an integer from 1 to 70 (preferably 1 to 20), or formula IV for example

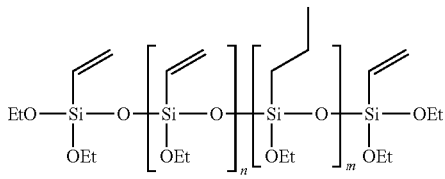

Formula IV

The vinyl siloxane units and the alkyl siloxane units in the above formulae may be present in the polymer as blocks, or randomly distributed, or in alternating positions. Alternatively, a polymer which has methoxy groups, or hydroxyl groups, in place of the ethoxy groups in formula IV is also a preferred embodiment.

The at least one polymer, in another type of embodiment, preferably comprises at least one silyl group containing polymer (i.e. at least one polymer containing multiple silyl groups), preferably having 500-10,000 dalton $MW_n$. In particular such polymer may be modified polybutadiene, especially silyl modified polybutadiene, preferably having 500-10,000 dalton $MW_n$. The at least one silyl group containing polymer preferably comprises trialkoxysilyl groups as the silyl groups (e.g. trimethoxysilyl or triethoxysilyl). The at least one silyl modified polybutadiene preferably comprises a trialkoxysilyl modified polybutadiene (the size of the trialkoxysilyl modified polybutadiene polymer (i.e. molecular weight, $MW_n$) is preferably 500-10,000 dalton). For example, the polybutadiene may be a trimethoxysilyl modified polybutadiene or a triethoxysilyl modified polybutadiene.

The silyl modified polybutadiene may have a nominal repeat unit of formula V:

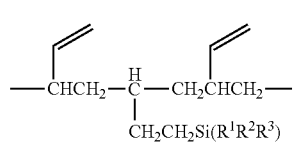

Formula V wherein $R^1$, $R^2$ and $R^3$ are independently selected from alkoxy, especially methoxy and ethoxy, hydroxyl, halo (especially Cl) and alkyl (especially C1-C3 alkyl, more especially methyl), provided that at least one of $R^1$, $R^2$ and $R^3$ is a leaving group (especially methoxy or ethoxy). $R^1$, $R^2$ and $R^3$ are preferably independently selected from alkoxy, especially methoxy and ethoxy, and hydroxyl. $R^1$, $R^2$ and $R^3$ are more preferably independently selected from alkoxy, especially methoxy and ethoxy. $R^1$, $R^2$ and $R^3$ are especially preferably the same, preferably both either methoxy or ethoxy.

In a preferred embodiment, the silyl modified polybutadiene may be an alkoxysilyl modified polybutadiene having a nominal repeat unit of formula VI:

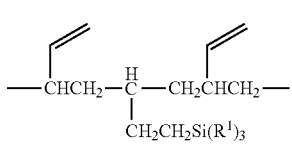

Formula VI wherein each $R^1$ is independently either methoxy or ethoxy. Preferably all $R^1$ are the same group.

For example:

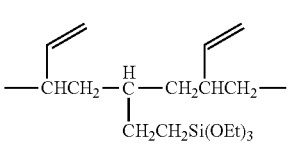

Formula VII

Alternatively, a polymer which has methoxy groups, or hydroxyl groups, in place of the ethoxy groups in formula VII is also a preferred embodiment.

In another preferred embodiment, the silyl modified polybutadiene may be an alkylalkoxysilyl modified polybutadiene. For example, the alkylalkoxysilyl modified polybutadiene may have a nominal repeat unit of formula VIII:

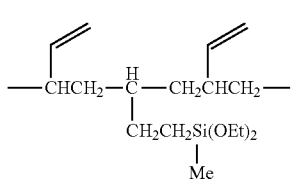

Formula III

Alternatively, a polymer which has methoxy groups, or hydroxyl groups, in place of the ethoxy groups in formula VIII is also a preferred embodiment.

A covalent attachment of the polymer of formula V, VI or VII to silica may yield a surface bound polymeric layer as follows, wherein vinyl reactive groups are present:

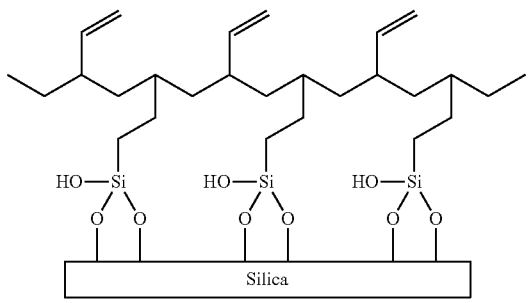

A covalent attachment of the polymer of formula VIII to silica may yield a surface bound polymeric layer as follows, wherein vinyl reactive groups are present:

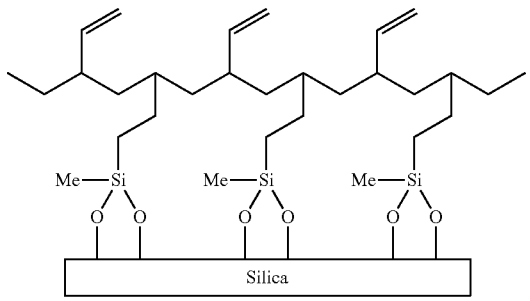

The use of the polymers described herein provide numerous benefits, for example: allowing multiple attachment to the substrate for stability whilst being controllable compared to very high MW polymers that may tend to clog pores in the substrate; allowing for subsequent surface modification with co-polymerization of allyl or vinyl functional compounds, wherein a "fixed" distance between adjacent reactive (e.g. vinyl) groups favors the formation of a more uniform protective layer on the substrate surface; and allowing flexibility in the stationary phase or column chemistry due to a choice of functional groups for attaching to the polymer.

Preferably, after the substrate is reacted with the polymer in the first reaction stage to form the layer covalently bound to the surface of the substrate (e.g. a layer with vinyl functionality), the substrate is then further reacted (further functionalized) with a silane (silane monomer, not polymer) also having the first reactive group, such as vinyl group. For example, a vinyl silane having alkyl and/or alkoxy groups may be used, such as vinyldimethylethoxysilane for instance. This helps to provide fuller coverage of the silica surface with reactive groups (vinyl groups) as the smaller monomers may fill in gaps between polymer molecules. The surface may then be reacted in the second stage functionalization.

The functionalizing compound for the second stage functionalization (i.e. functionalization of the first bonded layer) may be a polymeric or non-polymeric molecule, preferably a non-polymeric molecule. The functionalizing compound preferably comprises a group reactive with the reactive groups of the polymer (i.e. the first reactive groups). The reactive group of the functionalizing compound is herein termed second reactive group. In particular, a reactive olefinic group, or thiol, of the functionalizing compound is reactive with an olefinic group reactive group of the polymer. The second reactive group of the functionalizing compound is preferably a vinyl group, allyl group or a thiol group. Herein groups having double bonds, including vinyl, allyl, styrenics, acrylamides and acrylates, are within the scope of the term olefinic group.

The functionalizing compound comprises a functional group. The functional group advantageously provides a chromatographic functionality, e.g. reverse phase functionality. The functional group is preferably a hydrocarbyl group, more preferably alkyl or aryl, especially alkyl, such as C2-C30 alkyl, e.g. C18 alkyl. The alkyl may be substituted or unsubstituted alkyl, The aryl may be substituted or unsubstituted aryl. Any of those groups may optionally contain a heteroatoms in the form of a sulfur (S) and/or oxygen (O) linker, and/or may optionally contain a (primary, secondary, tertiary, or quaternary) amino group, sulfonamide, amide, carbamate, phosphonate, sulfonate and/or carboxylate group.

In one embodiment type, the functionalizing compound preferably is a hydrocarbon compound comprising an olefinic group or bond, especially an alkyl compound, preferably straight-chain alkyl, typically wherein the total carbon chain length is C4-C30, preferably C6-C22, more preferably C8-C22, still more preferably C8-C20, e.g. C8, C10, C12, C14, C16 or C18; or e.g. C9, C11, C13, C15, or C17. The hydrocarbon can be alkyl or aryl, substituted or unsubstituted. The alkyl compound is preferably an alkyl compound having a terminal olefinic group (e.g. an alkene) and a total chain length as aforesaid. Particularly preferred functionalizing compounds for the second stage functionalisation are thus C4-C30 alkene, preferably C6-C22 alkene, more preferably C8-C22 alkene, still more preferably C8-C20 alkene, e.g. C8, C10, C12, C14, C16 or C18 alkene, or allyl benzene; most preferably C8 alkene, C18 alkene, or allylbenzene. The double bond (olefinic group) of the alkene is preferably at a terminal position of the carbon chain, e.g. 1-octadecene; 1-octene.

The preferred alkene for the functionalizing compound, thus has a Formula IX:

Formula IX wherein $R_f$ is an alkyl group, especially C4-C30 alkyl, C6-C22 alkyl, C8-C22 alkyl, or C8-C20 alkyl.

In another embodiment type, the functionalizing compound preferably is an alkyl thiol or aryl thiol, especially alkyl thiol, typically wherein the total carbon chain length is C4-C30, preferably C4-C22, more preferably C14-C22, still more preferably C16-C20, e.g. C8, C10, C12, C14, C16 or C18; or e.g. C9, C11, C13, C15, or C17.

The invention also provides for the preparation of stationary phase material by functionalizing silica substrates using polymers under elevated temperature, preferably at reduced pressures, to form pH stable separation media. At least a first stage of reaction, i.e. reacting silica with at least one first functionalizing compound, is performed under elevated temperature at reduced pressures. Preferably a catalyst is also used and the reaction is performed in the absence of solvent (solvent free conditions).

In particular, the invention provides a method of forming a functionalized silica for chromatographic use comprising:

reacting silica with at least one first functionalizing compound under conditions of elevated reaction temperature (in particular above room temperature and preferably above 100 deg. C.) and reduced pressure (in particular below atmospheric pressure and preferably below 500 mbar), preferably in the absence of solvent;

the first functionalizing compound or compounds comprising one or more silyl groups for reacting with the surface of the silica and one or more first reactive groups (in particular one or more vinyl groups, allyl groups and/or one or more thiol groups), thereby covalently attaching the first functionalizing compound or compounds to the surface of the silica and leaving the first reactive groups unreacted; and reacting the one or more first reactive groups of the surface bound first functionalizing compound or compounds with at least one second functionalizing compound that comprises one or more second reactive groups reactive with the one or more first reactive groups (in particular one or more second reactive groups containing an olefinic bond and/or —SH (thiol) group) and that further comprises a functional group, in particular having chromatographic functionality, in particular alkyl or aryl, e.g. C18 alkyl. The at least one first functionalizing compound is preferably the polymer as herein described, i.e. the polymer for covalent attachment to the surface of the substrate, or in another embodiment may be a silane monomer (e.g. a vinylsilane). The polymer in particular may be of the type: siloxane polymer (e.g. vinyl siloxane polymer) or silyl modified polymer such as silyl modified polybutadiene, as herein described.

The second functionalizing compound is preferably the functionalizing compound herein described, i.e. a hydrocarbon compound comprising an olefinic group or bond, especially an alkyl compound, or is an alkyl thiol or aryl thiol as herein described.

The reaction conditions provided by the invention (elevated temperature, reduced pressure; optionally with catalyst; optionally with predeposition) provide numerous benefits, for example: the formation of stable bonding of the bonded polymeric layer; greater control of the thickness of the bonded polymeric layer; and reduced pore clogging, which is better for chromatography.

The second stage of reaction, i.e. reacting the one or more first reactive groups of the surface bound first functionalizing compound or compounds with at least one second functionalizing compound, need not be under reduced pressure although elevated temperature is desirable.

The elevated temperature for the first stage of reaction is preferably in the ranges: at least about 100° C., or at least about 110° C., or at least about 120° C., or at least about 140° C., or at least about 160° C., or at least about 180° C., or at least about 200° C., especially at least about 160° C., or at least about 180° C., or at least about 200° C.; especially the aforesaid ranges up to about 200° C., or up to about 220° C., or up to about 240° C., or up to about 260° C., or up to about 280° C., or up to about 300° C. More preferably, the elevated temperature for the first stage of reaction lies in the ranges about 200° C. to about 300° C., or about 210° C. to about 290° C., or about 220° C. to about 280° C., or about 230° C. to about 270° C., or about 250° C.

The reduced pressure for the first stage of reaction is preferably in the ranges: less than 500 mbar, more preferably less than 400 mbar, still more preferably less than 300 mbar, yet still more preferably less than 200 mbar, and most preferably less than 100 mbar. The pressure is preferably at least 0.01 mbar, more preferably at least 0.1 mbar, or at least 1 mbar.

The reduced pressure and the elevated temperature for the first stage of reaction are preferably applied concurrently at least for a period of time (first reaction period). This period of time may be at least 1 hour, or at least 2 hours, or at least 4 hours, or at least 8 hours, or at least 12 hours. The period of time may be up to 20 hours, or up to 30 hours. The elevated temperature is preferably applied for at least such period of time. The reduced pressure is preferably applied for substantially the same period as the elevated temperature.

The reaction is preferably catalyzed. The reaction medium therefore preferably comprises a catalyst in contact with the reactant species. A suitable known polymerization catalyst may be used. Particularly preferred catalysts are of organic amines, for example tetramethylethylenediamine.

The second stage of the process preferably provides polymer encapsulation of the silica phases using free radical polymerization of the polymeric layer. This polymerization is preferably performed in the presence of an initiator.

For the second stage of the process (encapsulated polymer layer from co-polymerization in the presence of an initiator), an elevated temperature is once again used. The pressure in the second stage can be atmospheric or ambient pressure or above, e.g. in the range from 1 to 2 atmospheres.

The elevated temperature for the second stage of reaction is preferably in the ranges: at least about 100° C., or at least about 110° C., or at least about 120° C., or at least about 140° C. 200° C.; especially the aforesaid ranges up to about 300° C., or up to about 200° C., or up to about 190° C., or up to about 180° C., or up to about 160° C. More preferably, the elevated temperature for the second stage of reaction lies in the ranges about 100° C. to about 300° C., or about 100° C. to about 200° C., or about 110° C. to about 190° C., or about 120° C. to about 180° C., or about 130° C. to about 170° C.

The elevated temperature for the second stage of reaction is preferably applied for a period of time (second reaction period). This period of time may be at least 1 hour, or at least 2 hours, or at least 4 hours, or at least 8 hours, or at least 12 hours. The period of time may be up to 20 hours, or up to 30 hours.

Both the first and second stages of reaction are preferably performed in an inert atmosphere, i.e. in an inert gas (e.g. nitrogen, or argon). The reactants are preferably purged with inert gas before applying the elevated temperature and, in the case of the first stage of reaction, before reducing the pressure. The inert atmosphere is then preferably maintained during the period of elevated temperature and, in the case of the first stage of reaction, reduced pressure. In another embodiment, where the reaction pressure is reduced to below 50 mbar, the reaction may be performed without an inert gas purge.

Preferably, the first stage of reaction is performed in the absence of an organic solvent. Preferably, the second stage of reaction is performed in the absence of an organic solvent. Any such solvent that may be used in a part of the process are preferably removed before the elevated reaction temperature is applied. The benefits of a solvent-free process, especially for polymerization for functionalization include: improved control over the surface modification; and improved control over the column chemistry. It should be noted that an absence of a solvent may be referred to as an absence of a liquid solvent or a liquid organic solvent.

Various reaction schemes may be used to implement the process of the invention. Numerous processing steps, including various optional steps, may be employed in the reaction schemes. The following illustration refers to silica but may be employed with other substrates.

The process may comprise a step of pre-treating the silica. The raw silica was acid-treated in 0.1M $HNO_3$ at 90° C. for 4 hours, then thoroughly rinsed with DI water until the filtrate was close to neutral. The acid-treated silica was dried under vacuum at 150° C. for at least 12 hrs and then stored in a desiccator.

The silica is preferably dried before it is subjected to a first stage of reaction.

The silica is preferably placed into a reaction vessel.

The process preferably comprises a first stage of reaction wherein the substrate is functionalized with first reactive groups, more preferably olefinic groups, especially vinyl groups. For the first stage, a first functionalizing compound is preferably added to the silica; the first functionalizing compound preferably being the polymer as herein described, i.e. the polymer for covalent attachment to the surface of the silica. A vinylalkoxysiloxane polymer is the most preferred. The first functionalizing compound when it is added may be contained in an organic solvent (e.g. methanol), which can be removed later.

A catalyst (e.g. an organic amine) for the first stage of reaction is preferably mixed with the silica and first functionalizing compound. Alternatively, a volatile catalyst may be used, which does not require to be mixed but rather is placed in the same reaction vessel as the silica.

Preferably, any volatile components, such as any organic solvent, may be removed, e.g. under reduced pressure. This may be performed either before or after adding a catalyst but preferably before adding a catalyst in order to avoid starting a reaction. In this way, the first stage of reaction is preferably performed under solvent free conditions.

After adding the first functionalizing compound and optionally catalyst, they may be mixed with the silica.

The components of silica, first functionalizing compound and catalyst are preferably flushed with an inert gas (e.g. nitrogen or argon) in a reaction vessel before reaction and preferably remain in the inert gas atmosphere during reaction.

The first stage of reaction is performed by heating the components in the reaction vessel (silica, first functionalizing compound and catalyst) to an elevated temperature for a first reaction period as described herein. In a preferred embodiment, the first stage of reaction is performed under reduced pressure, preferably less than 100 mbar (e.g. by evacuating the reaction vessel to the desired pressure).

The silica thereby functionalized with first reactive groups may then be filtered, washed and optionally dried.

The silica functionalized with first reactive groups may be optionally further reacted (i.e. further functionalized) with a silane (not polymer) having a first reactive group (e.g. vinyl), e.g. such as a vinyl silane of formula A, wherein the R groups are each independently alkoxy, hydroxyl, halo or alkyl:

Formula A

The silica thereby further functionalized with first reactive groups may then be filtered, washed and dried.

The process preferably comprises a second stage of reaction wherein the silica functionalized with the first reactive groups (vinyl groups) is reacted with a second functionalizing compound comprising a second reactive group (e.g. allyl group) and a functional group (e.g. alkyl group).

For the second stage, a second functionalizing compound is preferably added to the silica already functionalized with the first reactive groups (vinyl groups); the second functionalizing compound preferably being the C4-C30 alkene compound as herein described. A C8 or C18 alkene is most preferred, optionally with mixing. The second functionalizing compound may be mixed with the silica in an organic solvent (e.g. dichloromethane), which can be removed later.

An initiator (e.g. dicumyl peroxide) may be included in the mixture of second functionalizing compound and silica, e.g. to initiate free radical polymerization.

Preferably, any volatile components, such as any organic solvent, may be removed, e.g. under reduced pressure. In this way, the second stage of reaction is preferably performed under solvent free conditions.

The components of first functionalized silica, second functionalizing compound and initiator are preferably flushed with an inert gas (e.g. nitrogen or argon) in a reaction vessel before reaction and preferably remain in the inert gas atmosphere during the second stage of reaction.

The second stage of reaction is performed by heating the components in the reaction vessel (first functionalized silica, second functionalizing compound and initiator) to an elevated temperature (e.g. 50-300° C.) for a second reaction period as described herein. A functionalized polymer encapsulated silica is obtained. The silica may be optionally subjected to filtration and washing before use in a chromatography column.

The substrate (preferably a silica substrate) may be totally porous, superficially porous, or non-porous; and may be particulate or monolithic.

The substrate of the present invention is desirably a chromatographic material, or has chromatographic characteristics, for use, for example, in LC or SPE applications.

The substrate is preferably particulate wherein particles of the substrate are typically and preferably substantially spherical but may be irregular in shape in some embodiments. The particles preferably have a narrow size distribution.

In certain examples, the particles are essentially "monodisperse" or essentially "homodisperse", which indicates that the particle size of the majority of the particles (e.g., 80, 90 or 95% of the particles) does not vary substantially (e.g., not more than 10%) below or above the median particle size ($D_{50}$). In an exemplary monodisperse particle population, 90% of the particles have an average particle size of between about $0.9 \times D_{50}$ and about $1.1 \times D_{50}$. This is advantageous for chromatographic applications. Whilst monodispersed particles are preferred, particles with a broader particle size distribution may be useful in many applications.

The particles are typically microparticles, preferably 0.1 µm or larger in median particle diameter, preferably up to 1000 µm in median particle diameter. More preferably the particles are from 1 to 1000 µm, or 0.1 to 500 µm or 1 to 500 µm in diameter, or still more preferably 0.1 to 100 µm or 1 to 100 µm in diameter, or even more preferably 0.1 to 50 µm in diameter, especially 0.1 to 10 µm or 0.2 to 10 µm or 1 to 10 µm and most preferably 1.5 to 5 µm in diameter.

The particles may be porous (including partially porous, totally porous or superficially porous) or non-porous particles. The particles may be useful for preparing solid core chromatographic materials.

When porous particles are formed, the pores of the particles can be of any size. The nominal pore size is typically measured in angstroms ($10^{-10}$ m, Å). A pore size distribution (PSD) is calculated from adsorption data using the BJH (Barrett Joyner-Halenda) method and the average pore size ($W_{BJH}$) is defined as the maximum of the PSD. In one example, the average size or diameter of the pores is between about 1 and about 5000 Å, especially between about 50 and about 5000 Å. In another example, the volume average diameter of the pores is between about 10 and about 5000 Å, between about 10 and about 4000 Å, between about 10 and about 3000 Å, between about 10 and about 2000 Å, between about 10 and about 1000 Å, between about 10 and about 800 Å, between about 10 and about 600 Å, between about 10 and about 500 Å, between about 10 and about 400 Å, between about 10 and about 300 Å, between about 10 and about 200 Å, between about 10 and about 100 Å, between about 20 and about 2000 Å, between about 20 and about 1000 Å, between about 20 and about 500 Å, between about 20 and about 300 Å, between about 20 and about 200 Å, between about 20 and about 100 Å, between about 30 and about 2000 Å, between about 30 and about 1000 Å, between about 30 and about 500 Å, between about 30 and about 300 Å, between about 30 and about 200 Å, between about 30 and about 100 Å, between about 40 and about 2000 Å, between about 40 and about 1000 Å, between about 40 and about 500 Å, between about 40 and about 300 Å, between about 40 and about 200 Å, between about 40 and about 100 Å, between about 50 and about 2000 Å, between about 50 and about 1000 Å, between about 50 and about 500 Å, between about 50 and about 300 Å, between about 50 and about 200 Å, between about 50 and about 100 Å, between about 60 and about 2000 Å, between about 60 and about 1000 Å, between about 60 and about 500 Å, between about 60 and about 300 Å, between about 60 and about 200 Å, between about 60 and about 100 Å, between about 70 and about 2000 Å, between about 70 and about 1000 Å, between about 70 and about 500 Å, between about 70 and about 300 Å, between about 70 and about 200 Å, between about 70 and about 100 Å, between about 80 and about 2000 Å, between about 80 and about 1000 Å, between about 80 and about 500 Å, between about 80 and about 300 Å, between about 80 and about 200 Å, between about 100 and about 200 Å, between about 100 and about 300 Å, between about 100 and about 400 Å, between about 100 and about 500 Å, between about 200 and about 500 Å or between about 200 and about 600 Å. Preferably, the average pore size is between about 30 and about 2000 Å, more preferably between about 80 and about 1000 Å. Most preferably, the average pore size is between about 80 and about 300 Å.

The (BET) specific surface area of the particulate substrate material is typically between about 0.1 and about 2,000 m²/g, most typically between about 0.1 and about 1,000 m²/g. For example, the specific surface area of the particulate material is between about 1 and about 1,000 m²/g, between about 1 and about 800 m²/g, between about 1 and about 600 m²/g, between about 1 and about 500 m²/g, between about 1 and about 400 m²/g, between about 1 and about 200 m²/g or between about 1 and about 100 m²/g. In another example, the specific surface area of the material is between about 10 and about 1,000 m²/g, between about 10 and about 800 m²/g, between about 10 and about 600 m²/g, between about 10 and about 500 m²/g, between about 10 and about 400 m²/g, between about 10 and about 200 m²/g or between about 10 and about 100 m²/g. In another example, the specific surface area of the material is between about 50 and about 1,000 m²/g, between about 50 and about 800 m²/g, between about 50 and about 600 m²/g, between about 50 and about 500 m²/g, between about 50 and about 400 m²/g, between about 50 and about 200 m²/g or between about 50 and about 100 m²/g. Preferably, the specific surface area of the particulate material is between about 1 and about 500 m²/g, or between about 10 and about 500 m²/g (especially between about 50 and about 500 m²/g). In another example, the specific surface area more preferably is between about 10 and about 100 m²/g.

For non-porous particles, the specific surface area preferably is between about 0.5-10 m²/g. For non-porous particles, the median particle diameter is preferably from 0.1 to 5 µm.

In view of the detailed description above, numerous preferred types of materials may be realised, as indicated in table 1 below:

TABLE 1

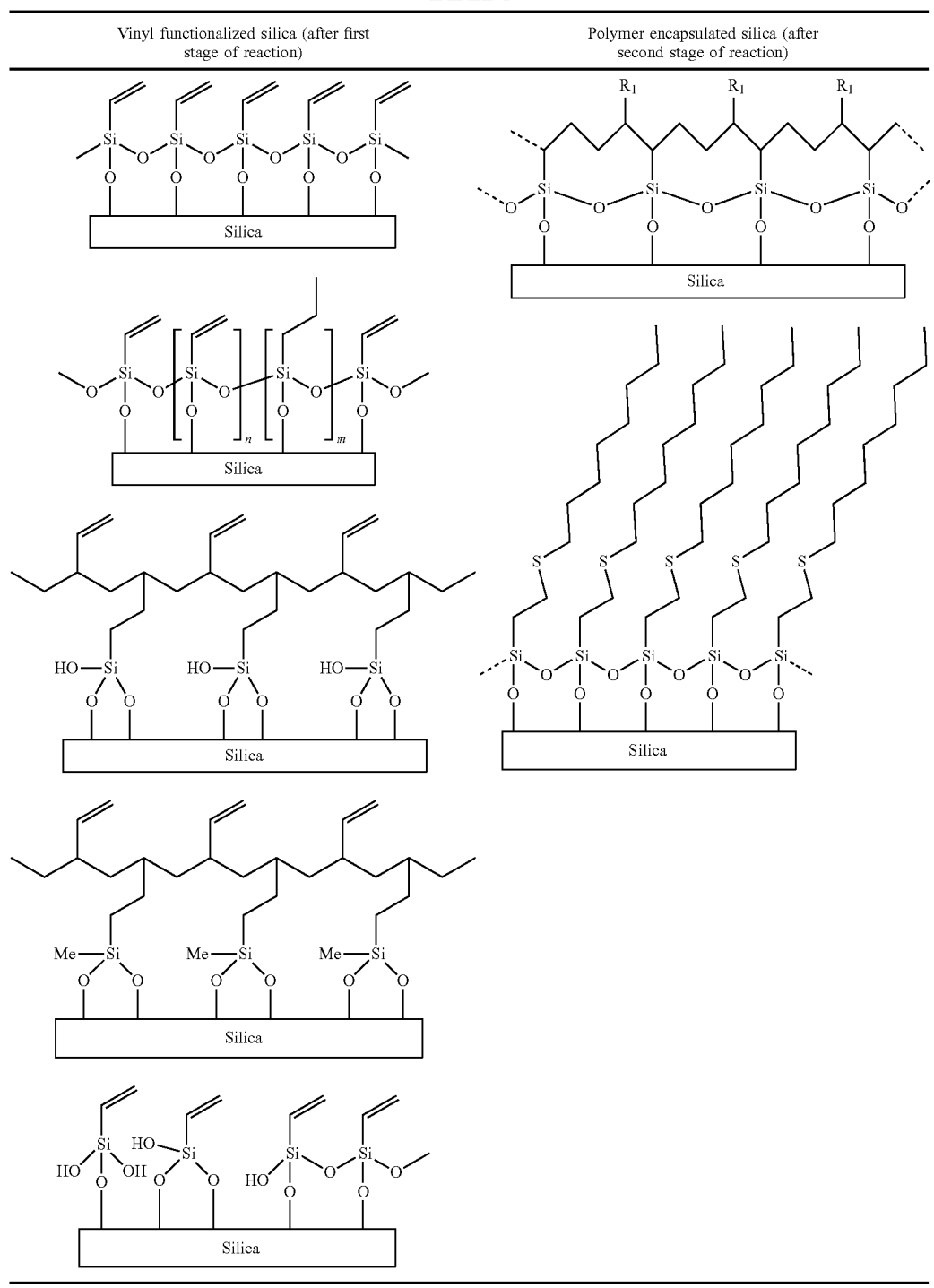

The material of the invention may be used in nano-LC, analytical-LC, or preparative scale LC, or SPE. In various embodiments, the material is disposed as a packed bed or monolith in a column. For example, a plastic or metal column is packed with the material.

The chromatographic material of the present invention may be used in a method of separating analytes comprising flowing a mobile phase containing a sample of the analytes through a column to chromatographically separate the analytes from each other, wherein the column is packed with the chromatographic material according to the present invention. Preferably, the pH of the mobile phase is about 11 or less and advantageously the pH of the mobile phase may be about 1 or less, which is typical when separating aminoglycoside antibiotics. Accordingly, the material may be used in a method of separating one or more aminoglycoside antibiotics from each other and/or from other components of a sample, the method comprising flowing a mobile phase containing a sample comprising one or more aminoglycoside antibiotics and optionally one or more other components through a column to chromatographically separate the one or more aminoglycoside antibiotics from each other and/or from one or more other components of the sample, wherein the column is packed with the chromatographic material according to the present invention. The pH of the mobile phase in such method is preferably about 1 or less. The method is preferably a method of separating a plurality of aminoglycoside antibiotics from each other from a sample comprising the plurality of aminoglycoside antibiotics.

The materials can provide a variety of high-performance characteristics. The materials exhibit exceptional stability under acidic conditions and greatly improved ruggedness under alkaline conditions. A column packed with such material is suitable for separating aminoglycoside antibiotics with excellent resolution and chemical ruggedness.

EXAMPLES

In order to enable further understanding of the invention, but without limiting the scope thereof, various exemplary and/or preferred embodiments of the invention are now described with reference to the accompanying drawings.

Example 1: Vinylalkoxysiloxane Polymers (FIG. 1)

Figure 2:
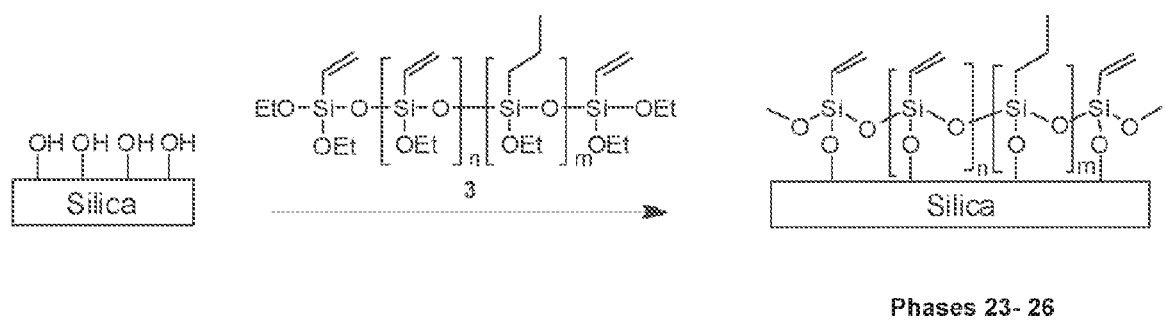
FIG. 2 (Scheme 2) shows a preparation of vinyl functionalized silica using vinyl silane co-polymer.

The vinylalkoxysiloxane polymers used in the Examples below were used as supplied by Gelest unless it is specified otherwise. FIG. 1 illustrates vinylmethoxysiloxane homopolymer 1: (Gelest, Cat #VMM-005) and vinylethoxysiloxane homopolymer 2: (Gelest, Cat #VEE-005). FIG. 2 illustrates vinylethoxysiloxane-propylethoxysiloxane copolymer 3: (Gelest, Cat #VPE-005).

Example 2: Preparation of Vinyl Functionalized Silica. Preparation of Vinylalkoxysiloxane Polymer Modified Phase in Solution (FIG. 1, Scheme 1)

Phase 10: 20 g of dried porous spherical silica particles ($d_p$, 3 μm; surface area, 225 m$^2$/g; pore size, 175 Å) were transferred into a 250-mL round bottom flask followed by the addition of a mixture of 5 g of vinylethoxysiloxane homopolymer 2 and 0.5 g of tetramethylethylenediamine (e.g.: Aldrich) in toluene (60 mL). After carefully dispersing above slurry, the reaction mixture was put under stable refluxing and stirred for 72 h. The silica particles were filtered and thoroughly washed with toluene and acetone. Next, the bonded silica was dispersed in a 100 mL mixture of 5% acetic acid solution (CH$_3$CN:H$_2$O=1:1, v/v) and sonicated for 2 h. After filtration and being washed with acetone, the resulting silica was dried under vacuum at 105° C. for overnight. The dried silica was re-dissolved in 60 mL of toluene followed by the addition of 5 g of vinyldimethylethoxysilane (e.g.: Gelest) and 0.5 g of tetramethylethylenediamine (e.g.: Aldrich). The resulting mixture was refluxed for 24 h. The functionalized silica particles were filtered and thoroughly washed with toluene and acetone to give Phase 10.

Phase 11: 20 g of dried porous spherical silica particles ($d_p$, 5 μm; surface area, 300 m$^2$/g; pore size, 120 Å) were transferred into a 250-mL round bottom flask followed by the addition of a mixture of 7 g of vinylethoxysiloxane homopolymer 2 and 0.5 g of tetramethylethylenediamine (e.g.: Aldrich) in toluene (60 mL). After carefully dispersing above slurry, the reaction mixture was put under stable refluxing and stirred for 72 h. The silica particles were filtered and thoroughly washed with toluene and acetone. Next, the bonded silica was dispersed in a 100 mL mixture of 5% acetic acid solution (CH$_3$CN:H$_2$O=1:1, v/v) and sonicated for 2 h. After filtration and being washed with acetone, the resulting silica was dried under vacuum at 105° C. for overnight. The dried silica was re-dissolved in 60 mL of toluene followed by the addition of 7 g of vinyldimethylethoxysilane (e.g.: Gelest) and 0.5 g of tetramethylethylenediamine (e.g.: Aldrich). The resulting mixture was refluxed for 24 h. The functionalized silica particles were filtered and thoroughly washed with toluene and acetone to give Phase 11.

Phase 12: 20 g of dried porous spherical silica particles ($d_p$, 5 μm; surface area, 225 m$^2$/g; pore size, 175 Å) were transferred into a 250-mL round bottom flask followed by the addition of a mixture of 5 g of vinylethoxysiloxane homopolymer 2 and 0.5 g of tetramethylethylenediamine (e.g.: Aldrich) in toluene (60 mL). After carefully dispersing above slurry, the reaction mixture was put under stable refluxing and stirred for 72 h. The silica particles were filtered and thoroughly washed with toluene and acetone. Next, the bonded silica was dispersed in a 100 mL mixture of 5% acetic acid solution (CH$_3$CN:H$_2$O=1:1, v/v) and sonicated for 2 h. After filtration and being washed with acetone, the resulting silica was dried under vacuum at 105° C. for overnight. The dried silica was re-dissolved in 60 mL of toluene followed by the addition of 5 g of vinyldimethylethoxysilane (e.g.: Gelest) and 0.5 g of tetramethylethylenediamine (e.g.: Aldrich). The resulting mixture was refluxed for 24 h. The functionalized silica particles were filtered and thoroughly washed with toluene and acetone to give Phase 12.

Phase 13: 20 g of dried porous spherical silica particles ($d_p$, 5 μm; surface area, 200 m$^2$/g; pore size, 200 Å) were transferred into a 250-mL round bottom flask followed by the addition of a mixture of 5 g of vinylethoxysiloxane homopolymer 2 and 0.5 g of tetramethylethylenediamine (e.g.: Aldrich) in toluene (60 mL). After carefully dispersing above slurry, the reaction mixture was put under stable refluxing and stirred for 72 h. The silica particles were filtered and thoroughly washed with toluene and acetone. Next, the bonded silica was dispersed in a 100 mL mixture of 5% acetic acid solution (CH$_3$CN:H$_2$O=1:1, v/v) and sonicated for 2 h. After filtration and being washed with acetone, the resulting silica was dried under vacuum at 105° C. for overnight. The dried silica was re-dissolved in 60 mL of toluene followed by the addition of 5 g of vinyldimethylethoxysilane (e.g.: Gelest) and 0.5 g of tetramethylethylenediamine (e.g.: Aldrich). The resulting mixture was refluxed for 24 h. The functionalized silica particles were filtered and thoroughly washed with toluene and acetone to give Phase 13.

Phase 14: 20 g of dried porous spherical silica particles ($d_p$, 5 μm; surface area, 30 m$^2$/g; pore size, 1000 Å) were transferred into a 250-mL round bottom flask followed by the addition of a mixture of 1.2 g of vinylethoxysiloxane homopolymer 2 and 0.1 g of tetramethylethylenediamine e.g.: Aldrich) in toluene (60 mL). After carefully dispersing above slurry, the reaction mixture was put under stable refluxing and stirred for 72 h. The silica particles were filtered and thoroughly washed with toluene and acetone. Next, the bonded silica was dispersed in a 100 mL mixture of 5% acetic acid solution (CH$_3$CN:H$_2$O=1:1, v/v) and sonicated for 2 h. After filtration and being washed with acetone, the resulting silica was dried under vacuum at 105° C. for overnight. The dried silica was re-dissolved in 60 mL of toluene followed by the addition of 1.2 g of vinyldimethylethoxysilane (e.g.: Gelest) and 0.1 g of tetramethylethylenediamine (e.g.: Aldrich). The resulting mixture was refluxed for 24 h. The functionalized silica particles were filtered and thoroughly washed with toluene and acetone to give Phase 14.

Example 3: Preparation of Vinyl Functionalized Silica. Preparation of Vinylalkoxysiloxane Polymer Modified Phase that was Initially Reacted in a Solvent-Free Condition at Elevated Temperature at 1 Atmosphere (Atm, FIG. 1, Scheme 1)

Phase 15: 20 g of dried porous spherical silica particles ($d_p$, 5 μm; surface area, 300 m$^2$/g; pore size, 120 Å) were transferred into a 250-mL round bottom flask followed by the addition of a solution of 7 g of vinylethoxysiloxane homopolymer 2 in a suitable solvent (e.g., methanol). The resulting mixture was sonicated to uniformity and then all volatiles were removed under reduced pressure. After a catalyst (e.g., 0.5 g of tetramethylethylenediamine) was added into the flask, the reaction mixture was put onto a rotary evaporator (i.e., rotavap) at 20 rpm and kept at 160° C. and 1 atm for 16 h. The resulting silica was dispersed into toluene (100 mL) and sonicated for 15 min, then filtered and thoroughly washed with toluene and acetone. The silica was dispersed in a 100 mL mixture of 5% acetic acid solution ($CH_3CN:H_2O=1:1$, v/v) and sonicated for 2 h. After filtration and being washed with acetone, the resulting silica was dried in under vacuum at 105° C. for overnight. The dried silica was dissolved in 60 mL of toluene followed by the addition of 7 g of vinyldimethylethoxysilane (e.g.: Gelest) and 0.5 g of tetramethylethylenediamine (e.g.: Aldrich). The resulting mixture was refluxed for 24 h. After cooling down, the silica particles were filtered and the cake was washed with toluene and acetone to give to Phase 15.

Phase 16: 20 g of dried porous spherical silica particles ($d_p$, 5 μm; surface area, 225 m$^2$/g; pore size, 175 Å) were transferred into a 250-mL round bottom flask followed by the addition of a solution of 5 g of vinylethoxysiloxane homopolymer 2 in a suitable solvent (e.g., methanol). The resulting mixture was sonicated to uniformity and then all volatiles were removed under reduced pressure. After a catalyst (e.g., 0.5 g of tetramethylethylenediamine) was added into the flask, the reaction mixture was put onto a rotavap at 20 rpm and kept at 160° C. and 1 atm for 16 h. The resulting silica was dispersed into toluene (100 mL) and sonicated for 15 min, then filtered and thoroughly washed with toluene and acetone. The silica was dispersed in a 100 mL mixture of 5% acetic acid solution ($CH_3CN:H_2O=1:1$, v/v) and sonicated for 2 h. After filtration and being washed with acetone, the resulting silica was dried in under vacuum at 105° C. for overnight. The dried silica was dissolved in 60 mL of toluene followed by the addition of 5 g of vinyldimethylethoxysilane (e.g.: Gelest) and 0.5 g of tetramethylethylenediamine (e.g.: Aldrich). The resulting mixture was refluxed for 24 h. After cooling down, the silica particles were filtered and the cake was washed with toluene and acetone to give to Phase 16.

Phase 17: 20 g of dried porous spherical silica particles ($d_p$, 5 μm; surface area, 200 m$^2$/g; pore size, 200 Å) were transferred into a 250-mL round bottom flask followed by the addition of a solution of 5 g of vinylethoxysiloxane homopolymer 2 in a suitable solvent (e.g., methanol). The resulting mixture was sonicated to uniformity and then all volatiles were removed under reduced pressure. After a catalyst (e.g., 0.5 g of tetramethylethylenediamine) was added into the flask, the reaction mixture was put onto a rotavap at 20 rpm and kept at 160° C. and 1 atm for 16 h. The resulting silica was dispersed into toluene (100 mL) and sonicated for 15 min, then filtered and thoroughly washed with toluene and acetone. The silica was dispersed in a 100 mL mixture of 5% acetic acid solution ($CH_3CN:H_2O=1:1$, v/v) and sonicated for 2 h. After filtration and being washed with acetone, the resulting silica was dried in under vacuum at 105° C. for overnight. The dried silica was dissolved in 60 mL of toluene followed by the addition of 5 g of vinyldimethylethoxysilane (e.g.: Gelest) and 0.5 g of tetramethylethylenediamine (e.g.: Aldrich). The resulting mixture was refluxed for 24 h. After cooling down, the silica particles were filtered and the cake was washed with toluene and acetone to give to Phase 17.

Phase 18: 20 g of dried porous spherical silica particles $d_p$, 5 μm; surface area, 30 m$^2$/g; pore size, 1000 Å) were transferred into a 250-mL round bottom flask followed by the addition of a solution of 1.2 g of vinylethoxysiloxane homopolymer 2 in a suitable solvent (e.g., methanol). The resulting mixture was sonicated to uniformity and then all volatiles were removed under reduced pressure. After a catalyst (e.g., 0.1 g of tetramethylethylenediamine) was added into the flask, the reaction mixture was put onto a rotavap at 20 rpm and kept at 160° C. and 1 atm for 16 h. The resulting silica was dispersed into toluene (100 mL) and sonicated for 15 min, then filtered and thoroughly washed with toluene and acetone. The silica was dispersed in a 100 mL mixture of 5% acetic acid solution ($CH_3CN:H_2O=1:1$, v/v) and sonicated for 2 h. After filtration and being washed with acetone, the resulting silica was dried in under vacuum at 105° C. for overnight. The dried silica was dissolved in 60 mL of toluene followed by the addition of 1.2 g of vinyldimethylethoxysilane (e.g.: Gelest) and 0.1 g of tetramethylethylenediamine (e.g.: Aldrich). The resulting mixture was refluxed for 24 h. After cooling down, the silica particles were filtered and the cake was washed with toluene and acetone to give to Phase 18.

Example 4: Preparation of Vinyl Functionalized Silica. Preparation of Vinylalkoxysiloxane Polymer Modified Phase in Solvent-Free Condition at Elevated Temperature and Reduced Pressure (FIG. 1, Scheme 1)

Phase 19: 20 g of dried porous spherical silica particles ($d_p$, 5 μm; surface area, 300 m$^2$/g; pore size, 120 Å) were transferred into a 250-mL round bottom flask followed by the addition of a solution of 7 g of vinylethoxysiloxane homopolymer 2 in a suitable solvent (e.g., methanol). The resulting mixture was sonicated to uniformity and then all volatiles were completely removed under reduced pressure. The dried mixture was placed into the reactor equipped with heating and vacuum capacity. After placing a catalyst (e.g., 0.5 g of tetramethylethylenediamine) into the reactor the reactor was sealed followed by flushing with an inert gas (e.g., nitrogen or argon) for 30 min. Next, the reactor was evacuated with a vacuum pump to a certain value (e.g. below 100 mbar). The reactor was heated to a desired temperature (>100° C.) and kept at the same temperature for 16 h. After cooling down, the silica particles were dispersed in toluene (100-mL) and sonicated for 30 min. After filtration, the cake was washed with toluene and acetone. The resulting silica was dispersed in a mixture of 5% acetic acid solution ($CH_3CN:H_2O=1:1$, v/v) and allowed to stand for 12 h. After filtration and being washed with acetone, the resulting silica was dried under vacuum at 105° C. for 12 h. The dried silica was placed again into the reactor equipped with heating and vacuum capacity. After placing a catalyst (e.g., 0.5 g of tetramethylethylenediamine) and 7 g of vinyldimethylethoxysilane into the reactor, the reactor was sealed followed by flushing with an inert gas (e.g., nitrogen or argon) for 30 min. Next, the reactor was evacuated with a vacuum pump to a desired value (e.g. below 100 mbar). The reactor was heated to a desired temperature (>100° C.) and kept at the same temperature for 16 h. After cooling down, the silica particles were dispersed in toluene (100-mL) and sonicated for 30 min. After filtration, the cake was washed with toluene and acetone to give to Phase 19.

Phase 20: 20 g of dried porous spherical silica particles ($d_p$, 5 μm; surface area, 225 m$^2$/g; pore size, 175 Å) were transferred into a 250-mL round bottom flask followed by the addition of a solution of 5 g of vinylethoxysiloxane homopolymer 2 in a suitable solvent (e.g., methanol). The resulting mixture was sonicated to uniformity and then all volatiles were completely removed under reduced pressure. The dried mixture was placed into the reactor equipped with heating and vacuum capacity. After placing a catalyst (e.g., 0.5 g of tetramethylethylenediamine) into the reactor the reactor was sealed followed by flushing with an inert gas (e.g., nitrogen or argon) for 30 min. Next, the reactor was evacuated with a vacuum pump to a certain value (e.g. below 100 mbar). The reactor was heated to a desired temperature (>100° C.) and kept at the same temperature for 16 h. After cooling down, the silica particles were dispersed in toluene (100-mL) and sonicated for 30 min. After filtration, the cake was washed with toluene and acetone. The resulting silica was dispersed in a mixture of 5% acetic acid solution ($CH_3CN:H_2O$=1:1, v/v) and allowed to stand for 12 h. After filtration and being washed with acetone, the resulting silica was dried under vacuum at 105° C. for 12 h. The dried silica was placed again into the reactor equipped with heating and vacuum capacity. After placing a catalyst (e.g., 0.5 g of tetramethylethylenediamine) and 5 g of vinyldimethylethoxysilane into the reactor, the reactor was sealed followed by flushing with an inert gas (e.g., nitrogen or argon) for 30 min. Next, the reactor was evacuated with a vacuum pump to a desired value (e.g. below 100 mbar). The reactor was heated to a desired temperature (>100° C.) and kept at the same temperature for 16 h. After cooling down, the silica particles were dispersed in toluene (100-mL) and sonicated for 30 min. After filtration, the cake was washed with toluene and acetone to give to Phase 20.

Phase 21: 20 g of dried porous spherical silica particles ($d_p$, 5 μm; surface area, 200 m$^2$/g; pore size, 200 Å) were transferred into a 250-mL round bottom flask followed by the addition of a solution of 5 g of vinylethoxysiloxane homopolymer 2 in a suitable solvent (e.g., methanol). The resulting mixture was sonicated to uniformity and then all volatiles were completely removed under reduced pressure. The dried mixture was placed into the reactor equipped with heating and vacuum capacity. After placing a catalyst (e.g., 0.5 g of tetramethylethylenediamine) into the reactor the reactor was sealed followed by flushing with an inert gas (e.g., nitrogen or argon) for 30 min. Next, the reactor was evacuated with a vacuum pump to a certain value (e.g. below 100 mbar). The reactor was heated to a desired temperature (>100° C.) and kept at the same temperature for 16 h. After cooling down, the silica particles were dispersed in toluene (100-mL) and sonicated for 30 min. After filtration, the cake was washed with toluene and acetone. The resulting silica was dispersed in a mixture of 5% acetic acid solution ($CH_3CN:H_2O$=1:1, v/v) and allowed to stand for 12 h. After filtration and being washed with acetone, the resulting silica was dried under vacuum at 105° C. for 12 h. The dried silica was placed again into the reactor equipped with heating and vacuum capacity. After placing a catalyst (e.g., 0.5 g of tetramethylethylenediamine) and 5 g of vinyldimethylethoxysilane into the reactor, the reactor was sealed followed by flushing with an inert gas (e.g., nitrogen or argon) for 30 min. Next, the reactor was evacuated with a vacuum pump to a desired value (e.g. below 100 mbar). The reactor was heated to a desired temperature (>100° C.) and kept at the same temperature for 16 h. After cooling down, the silica particles were dispersed in toluene (100-mL) and sonicated for 30 min. After filtration, the cake was washed with toluene and acetone to give to Phase 21.

Phase 22: 20 g of dried porous spherical silica particles ($d_p$, 5 μm; surface area, 30 m$^2$/g; pore size, 1000 Å) were transferred into a 250-mL round bottom flask followed by the addition of a solution of 1.2 g of vinylethoxysiloxane homopolymer 2 in a suitable solvent (e.g., methanol). The resulting mixture was sonicated to uniformity and then all volatiles were completely removed under reduced pressure. The dried mixture was placed into the reactor equipped with heating and vacuum capacity. After placing a catalyst (e.g., 0.1 g of tetramethylethylenediamine) into the reactor the reactor was sealed followed by flushing with an inert gas (e.g., nitrogen or argon) for 30 min. Next, the reactor was evacuated with a vacuum pump to a certain value (e.g. below 100 mbar). The reactor was heated to a desired temperature (>100° C.) and kept at the same temperature for 16 h. After cooling down, the silica particles were dispersed in toluene (100-mL) and sonicated for 30 min. After filtration, the cake was washed with toluene and acetone. The resulting silica was dispersed in a mixture of 5% acetic acid solution ($CH_3CN:H_2O$=1:1, v/v) and allowed to stand for 12 h. After filtration and being washed with acetone, the resulting silica was dried under vacuum at 105° C. for 12 h. The dried silica was placed again into the reactor equipped with heating and vacuum capacity. After placing a catalyst (e.g., 0.1 g of tetramethylethylenediamine) and 1.2 g of vinyldimethylethoxysilane into the reactor, the reactor was sealed followed by flushing with an inert gas (e.g., nitrogen or argon) for 30 min. Next, the reactor was evacuated with a vacuum pump to a desired value (e.g. below 100 mbar). The reactor was heated to a desired temperature (>100° C.) and kept at the same temperature for 16 h. After cooling down, the silica particles were dispersed in toluene (100-mL) and sonicated for 30 min. After filtration, the cake was washed with toluene and acetone to give to Phase 22.

Example 5: Preparation of Vinyl Functionalized Silica. Preparation of Vinylalkoxysiloxane Co-Polymer 3 Modified Phase in Solvent-Free Condition at Elevated Temperature and Reduced Pressure (FIG. 2, Scheme 2)

Phase 23: 20 g of dried porous spherical silica particles ($d_p$, 5 μm; surface area, 300 m$^2$/g; pore size, 120 Å) were transferred into a 250-mL round bottom flask followed by the addition of a solution of 7 g of vinylethoxysiloxane-propylethoxysiloxane copolymer 3 in a suitable solvent (e.g., methanol). The resulting mixture was sonicated to uniformity and then all volatiles were completely removed under reduced pressure. The dried mixture was placed into the reactor equipped with heating and vacuum capacity. After placing a catalyst (e.g., 0.5 g of tetramethylethylenediamine) into the reactor the reactor was sealed followed by flushing with an inert gas (e.g., nitrogen or argon) for 30 min. Next, the reactor was evacuated with a vacuum pump to a certain value (e.g. below 100 mbar). The reactor was heated to a desired temperature (>100° C.) and kept at the same temperature for 16 h. After cooling down, the silica particles were dispersed in toluene (100-mL) and sonicated for 30 min. After filtration, the cake was washed with toluene and acetone. The resulting silica was dispersed in a mixture of 5% acetic acid solution ($CH_3CN:H_2O=1:1$, v/v) and allowed to stand for 12 h. After filtration and being washed with acetone, the resulting silica was dried under vacuum at 105° C. for 12 h. The dried silica was placed again into the reactor equipped with heating and vacuum capacity. After placing a catalyst (e.g., 0.5 g of tetramethylethylenediamine) and 7 g of vinyldimethylethoxysilane into the reactor, the reactor was sealed followed by flushing with an inert gas (e.g., nitrogen or argon) for 30 min. Next, the reactor was evacuated with a vacuum pump to a desired value (e.g. below 100 mbar). The reactor was heated to a desired temperature (>100° C.) and kept at the same temperature for 16 h. After cooling down, the silica particles were dispersed in toluene (100-mL) and sonicated for 30 min. After filtration, the cake was washed with toluene and acetone to give to Phase 23.

Phase 24: 20 g of dried porous spherical silica particles ($d_p$, 5 μm; surface area, 225 m$^2$/g; pore size, 175 Å) were transferred into a 250-mL round bottom flask followed by the addition of a solution of 5 g of vinylethoxysiloxane-propylethoxysiloxane copolymer 3 in a suitable solvent (e.g., methanol). The resulting mixture was sonicated to uniformity and then all volatiles were completely removed under reduced pressure. The dried mixture was placed into the reactor equipped with heating and vacuum capacity. After placing a catalyst (e.g., 0.5 g of tetramethylethylenediamine) the reactor was sealed followed by flushing with an inert gas (e.g., nitrogen or argon) for 30 min. Next, the reactor was evacuated with a vacuum pump to a certain value (e.g. below 100 mbar). The reactor was heated to a desired temperature (>100° C.) and kept at the same temperature for 16 h. After cooling down, the silica particles were dispersed in toluene (100-mL) and sonicated for 30 min. After filtration, the cake was washed with toluene and acetone. The resulting silica was dispersed in a mixture of 5% acetic acid solution ($CH_3CN:H_2O=1:1$, v/v) and allowed to stand for 12 h. After filtration and being washed with acetone, the resulting silica was dried under vacuum at 105° C. for 12 h. The dried silica was placed again into the reactor equipped with heating and vacuum capacity. After placing a catalyst (e.g., 0.5 g of tetramethylethylenediamine) and 5 g of vinyldimethylethoxysilane into the reactor, the reactor was sealed followed by flushing with an inert gas (e.g., nitrogen or argon) for 30 min. Next, the reactor was evacuated with a vacuum pump to a desired value (e.g. below 100 mbar). The reactor was heated to a desired temperature (>100° C.) and kept at the same temperature for 16 h. After cooling down, the silica particles were dispersed in toluene (100-mL) and sonicated for 30 min. After filtration, the cake was washed with toluene and acetone to give to Phase 24.

Phase 25: 20 g of dried porous spherical silica particles ($d_p$, 5 μm; surface area, 200 m$^2$/g; pore size, 200 Å) were transferred into a 250-mL round bottom flask followed by the addition of a solution of 5 g of vinylethoxysiloxane-propylethoxysiloxane copolymer 3 in a suitable solvent (e.g., methanol). The resulting mixture was sonicated to uniformity and then all volatiles were completely removed under reduced pressure. The dried mixture was placed into the reactor equipped with heating and vacuum capacity. After placing a catalyst (e.g., 0.5 g of tetramethylethylenediamine) into the reactor the reactor was sealed followed by flushing with an inert gas (e.g., nitrogen or argon) for 30 min. Next, the reactor was evacuated with a vacuum pump to a certain value (e.g. below 100 mbar). The reactor was heated to a desired temperature (>100° C.) and kept at the same temperature for 16 h. After cooling down, the silica particles were dispersed in toluene (100-mL) and sonicated for 30 min. After filtration, the cake was washed with toluene and acetone. The resulting silica was dispersed in a mixture of 5% acetic acid solution ($CH_3CN:H_2O=1:1$, v/v) and allowed to stand for 12 h. After filtration and being washed with acetone, the resulting silica was dried under vacuum at 105° C. for 12 h. The dried silica was placed again into the reactor equipped with heating and vacuum capacity. After placing a catalyst (e.g., 0.5 g of tetramethylethylenediamine) and 5 g of vinyldimethylethoxysilane into the reactor, the reactor was sealed followed by flushing with an inert gas (e.g., nitrogen or argon) for 30 min. Next, the reactor was evacuated with a vacuum pump to a desired value (e.g. below 100 mbar). The reactor was heated to a desired temperature (>100° C.) and kept at the same temperature for 16 h. After cooling down, the silica particles were dispersed in toluene (100-mL) and sonicated for 30 min. After filtration, the cake was washed with toluene and acetone to give to Phase 25.

Phase 26: 20 g of dried porous spherical silica particles ($d_p$, 5 μm; surface area, 30 m$^2$/g; pore size, 1000 Å) were transferred into a 250-mL round bottom flask followed by the addition of a solution of 1.2 g of vinylethoxysiloxane-propylethoxysiloxane copolymer 3 in a suitable solvent (e.g., methanol). The resulting mixture was sonicated to uniformity and then all volatiles were completely removed under reduced pressure. The dried mixture was placed into the reactor equipped with heating and vacuum capacity. After placing a catalyst (e.g., 0.1 g of tetramethylethylenediamine) into the reactor the reactor was sealed followed by flushing with an inert gas (e.g., nitrogen or argon) for 30 min. Next, the reactor was evacuated with a vacuum pump to a certain value (e.g. below 100 mbar). The reactor was heated to a desired temperature (>100° C.) and kept at the same temperature for 16 h. After cooling down, the silica particles were dispersed in toluene (100-mL) and sonicated for 30 min. After filtration, the cake was washed with toluene and acetone. The resulting silica was dispersed in a mixture of 5% acetic acid solution ($CH_3CN:H_2O=1:1$, v/v) and allowed to stand for 12 h. After filtration and being washed with acetone, the resulting silica was dried under vacuum at 105° C. for 12 h. The dried silica was placed again into the reactor equipped with heating and vacuum capacity. After placing a catalyst (e.g., 0.1 g of tetramethylethylenediamine) and 1.2 g of vinyldimethylethoxysilane into the reactor, the reactor was sealed followed by flushing with an inert gas (e.g., nitrogen or argon) for 30 min. Next, the reactor was evacuated with a vacuum pump to a desired value (e.g. below 100 mbar). The reactor was heated to a desired temperature (>100° C.) and kept at the same temperature for 16 h. After cooling down, the silica particles were dispersed in toluene (100-mL) and sonicated for 30 min. After filtration, the cake was washed with toluene and acetone to give to Phase 26.

Figure 3:
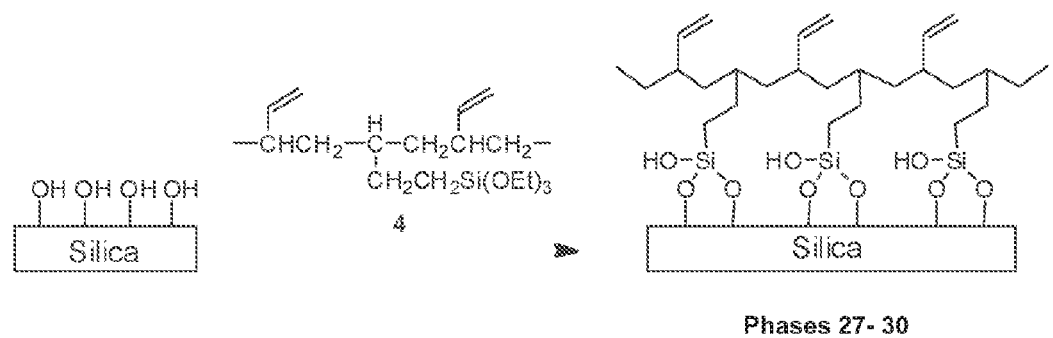
FIG. 3 (Scheme 3) shows a preparation of vinyl functionalized silica using triethoxysilyl modified polybutadiene.
Figure 4:
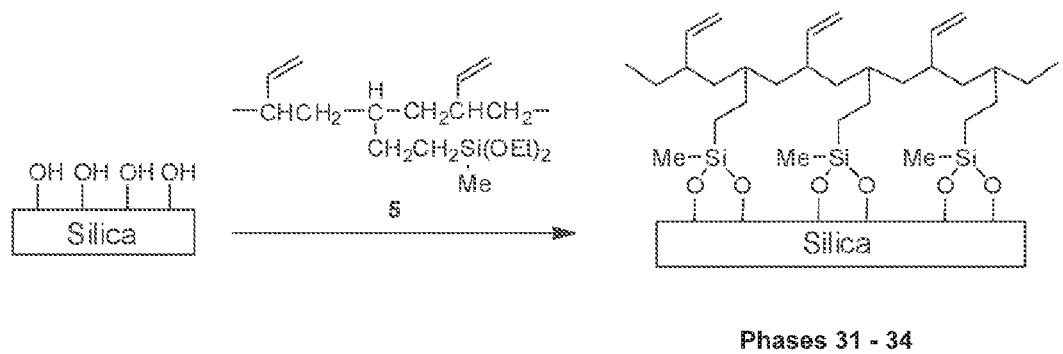
FIG. 4 (Scheme 4) shows a preparation of vinyl functionalized silica using diethoxymethylsilyl modified polybutadiene.

Example 6: Preparation of Vinyl Functionalized Silica. Preparation of Polybutadiene Modified Phase in Solvent-Free Condition at Elevated Temperature at Reduced Pressure (FIGS. 3 and 4, Schemes 3 and 4)

Phase 27: 20 g of dried porous spherical silica particles ($d_p$, 5 μm; surface area, 300 m$^2$/g; pore size, 120 Å) were transferred into a 250-mL round bottom flask followed by the addition of a solution of 13.5 g of triethoxysilyl modified poly-1,2-butadiene 4 (Gelest, Cat #SSP-055) in a suitable solvent (e.g., methanol). The resulting mixture was sonicated to uniformity and then all volatiles were completely removed under reduced pressure. The dried mixture was placed into the reactor equipped with heating and vacuum capacity. After placing a catalyst (e.g., 0.5 g of tetramethylethylenediamine) into the reactor the reactor was sealed followed by flushing with an inert gas (e.g., nitrogen or argon) for 30 min. Next, the reactor was evacuated with a vacuum pump to a certain value (e.g. below 100 mbar). The reactor was heated to a desired temperature (>100° C.) and kept at the same temperature for 16 h. After cooling down, the silica particles were dispersed in toluene (100-mL) and sonicated for 30 min. After filtration, the cake was washed with toluene and acetone. The resulting silica was dispersed in a mixture of 5% acetic acid solution ($CH_3CN:H_2O=1:1$, v/v) and allowed to stand for 12 h. After filtration and being washed with acetone, the resulting silica was dried under vacuum at 105° C. for 12 h. The dried silica was placed again into the reactor equipped with heating and vacuum capacity. After placing a catalyst (e.g., 0.5 g of tetramethylethylenediamine) and 7 g of vinyldimethylethoxysilane into the reactor, the reactor was sealed followed by flushing with an inert gas (e.g., nitrogen or argon) for 30 min. Next, the reactor was evacuated with a vacuum pump to a desired value (e.g. below 100 mbar). The reactor was heated to a desired temperature (>100° C.) and kept at the same temperature for 16 h. After cooling down, the silica particles were dispersed in toluene (100-mL) and sonicated for 30 min. After filtration, the cake was washed with toluene and acetone to give to Phase 27.

Phase 28: 20 g of dried porous spherical silica particles ($d_p$, 5 μm; surface area, 225 m$^2$/g; pore size, 175 Å) were transferred into a 250-mL round bottom flask followed by the addition of a solution of 9.6 g of triethoxysilyl modified poly-1,2-butadiene 4 (Gelest, Cat #SSP-055) in a suitable solvent (e.g., methanol). The resulting mixture was sonicated to uniformity and then all volatiles were completely removed under reduced pressure. The dried mixture was placed into the reactor equipped with heating and vacuum capacity. After placing a catalyst (e.g., 0.5 g of tetramethylethylenediamine) into the reactor the reactor was sealed followed by flushing with an inert gas (e.g., nitrogen or argon) for 30 min. Next, the reactor was evacuated with a vacuum pump to a certain value (e.g. below 100 mbar). The reactor was heated to a desired temperature (>100° C.) and kept at the same temperature for 16 h. After cooling down, the silica particles were dispersed in toluene (100-mL) and sonicated for 30 min. After filtration, the cake was washed with toluene and acetone. The resulting silica was dispersed in a mixture of 5% acetic acid solution ($CH_3CN:H_2O=1:1$, v/v) and allowed to stand for 12 h. After filtration and being washed with acetone, the resulting silica was dried under vacuum at 105° C. for 12 h. The dried silica was placed again into the reactor equipped with heating and vacuum capacity. After placing a catalyst (e.g., 0.5 g of tetramethylethylenediamine) and 5 g of vinyldimethylethoxysilane into the reactor, the reactor was sealed followed by flushing with an inert gas (e.g., nitrogen or argon) for 30 min. Next, the reactor was evacuated with a vacuum pump to a desired value (e.g. below 100 mbar). The reactor was heated to a desired temperature (>100° C.) and kept at the same temperature for 16 h. After cooling down, the silica particles were dispersed in toluene (100-mL) and sonicated for 30 min. After filtration, the cake was washed with toluene and acetone to give to Phase 28.

Phase 29: 20 g of dried porous spherical silica particles ($d_p$, 5 μm; surface area, 200 m$^2$/g; pore size, 200 Å) were transferred into a 250-mL round bottom flask followed by the addition of a solution of 9.6 g of triethoxysilyl modified poly-1,2-butadiene 4 (Gelest, Cat #SSP-055) in a suitable solvent (e.g., methanol). The resulting mixture was sonicated to uniformity and then all volatiles were completely removed under reduced pressure. The dried mixture was placed into the reactor equipped with heating and vacuum capacity. After placing a catalyst (e.g., 0.5 g of tetramethylethylenediamine) into the reactor the reactor was sealed followed by flushing with an inert gas (e.g., nitrogen or argon) for 30 min. Next, the reactor was evacuated with a vacuum pump to a certain value (e.g. below 100 mbar). The reactor was heated to a desired temperature (>100° C.) and kept at the same temperature for 16 h. After cooling down, the silica particles were dispersed in toluene (100-mL) and sonicated for 30 min. After filtration, the cake was washed with toluene and acetone. The resulting silica was dispersed in a mixture of 5% acetic acid solution ($CH_3CN:H_2O=1:1$, v/v) and allowed to stand for 12 h. After filtration and being washed with acetone, the resulting silica was dried under vacuum at 105° C. for 12 h. The dried silica was placed again into the reactor equipped with heating and vacuum capacity. After placing a catalyst (e.g., 0.5 g of tetramethylethylenediamine) and 5 g of vinyldimethylethoxysilane into the reactor, the reactor was sealed followed by flushing with an inert gas (e.g., nitrogen or argon) for 30 min. Next, the reactor was evacuated with a vacuum pump to a desired value (e.g. below 100 mbar). The reactor was heated to a desired temperature (>100° C.) and kept at the same temperature for 16 h. After cooling down, the silica particles were dispersed in toluene (100-mL) and sonicated for 30 min. After filtration, the cake was washed with toluene and acetone to give to Phase 29.

Phase 30: 20 g of dried porous spherical silica particles ($d_p$, 5 μm; surface area, 30 m$^2$/g; pore size, 1000 Å) were transferred into a 250-mL round bottom flask followed by the addition of a solution of 2.4 g of triethoxysilyl modified poly-1,2-butadiene 4 (Gelest, Cat #SSP-055) in a suitable solvent (e.g., methanol). The resulting mixture was sonicated to uniformity and then all volatiles were completely removed under reduced pressure. The dried mixture was placed into the reactor equipped with heating and vacuum capacity. After placing a catalyst (e.g., 0.1 g of tetramethylethylenediamine) into the reactor the reactor was sealed followed by flushing with an inert gas (e.g., nitrogen or argon) for 30 min. Next, the reactor was evacuated with a vacuum pump to a certain value (e.g. below 100 mbar). The reactor was heated to a desired temperature (>100° C.) and kept at the same temperature for 16 h. After cooling down, the silica particles were dispersed in toluene (100-mL) and sonicated for 30 min. After filtration, the cake was washed with toluene and acetone. The resulting silica was dispersed in a mixture of 5% acetic acid solution ($CH_3CN:H_2O=1:1$, v/v) and allowed to stand for 12 h. After filtration and being washed with acetone, the resulting silica was dried under vacuum at 105° C. for 12 h. The dried silica was placed again into the reactor equipped with heating and vacuum capacity. After placing a catalyst (e.g., 0.1 g of tetramethylethylenediamine) and 1.2 g of vinyldimethylethoxysilane into the reactor, the reactor was sealed followed by flushing with an inert gas (e.g., nitrogen or argon) for 30 min. Next, the reactor was evacuated with a vacuum pump to a desired value (e.g. below 100 mbar). The reactor was heated to a desired temperature (>100° C.) and kept at the same temperature for 16 h. After cooling down, the silica particles were dispersed in toluene (100-mL) and sonicated for 30 min. After filtration, the cake was washed with toluene and acetone to give to Phase 30.

Phase 31: 20 g of dried porous spherical silica particles ($d_p$, 5 µm; surface area, 300 m$^2$/g; pore size, 120 Å) were transferred into a 250-mL round bottom flask followed by the addition of a solution of 13.5 g of diethoxymethylsilyl modified poly-1,2-butadiene 5 (Gelest, Cat #SSP-058) in a suitable solvent (e.g., methanol). The resulting mixture was sonicated to uniformity and then all volatiles were completely removed under reduced pressure. The dried mixture was placed into the reactor equipped with heating and vacuum capacity. After placing a catalyst (e.g., 0.5 g of tetramethylethylenediamine) into the reactor the reactor was sealed followed by flushing with an inert gas (e.g., nitrogen or argon) for 30 min. Next, the reactor was evacuated with a vacuum pump to a certain value (e.g. below 100 mbar). The reactor was heated to a desired temperature (>100° C.) and kept at the same temperature for 16 h. After cooling down, the silica particles were dispersed in toluene (100-mL) and sonicated for 30 min. After filtration, the cake was washed with toluene and acetone. The resulting silica was dispersed in a mixture of 5% acetic acid solution (CH$_3$CN:H$_2$O=1:1, v/v) and allowed to stand for 12 h. After filtration and being washed with acetone, the resulting silica was dried under vacuum at 105° C. for 12 h. The dried silica was placed again into the reactor equipped with heating and vacuum capacity. After placing a catalyst (e.g., 0.5 g of tetramethylethylenediamine) and 7 g of vinyldimethylethoxysilane into the reactor, the reactor was sealed followed by flushing with an inert gas (e.g., nitrogen or argon) for 30 min. Next, the reactor was evacuated with a vacuum pump to a desired value (e.g. below 100 mbar). The reactor was heated to a desired temperature (>100° C.) and kept at the same temperature for 16 h. After cooling down, the silica particles were dispersed in toluene (100-mL) and sonicated for 30 min. After filtration, the cake was washed with toluene and acetone to give to Phase 31.

Phase 32: 20 g of dried porous spherical silica particles ($d_p$, 5 µm; surface area, 225 m$^2$/g; pore size, 175 Å) were transferred into a 250-mL round bottom flask followed by the addition of a solution of 9.6 g of diethoxymethylsilyl modified poly-1,2-butadiene 5 (Gelest, Cat #SSP-058) in a suitable solvent (e.g., methanol). The resulting mixture was sonicated to uniformity and then all volatiles were completely removed under reduced pressure. The dried mixture was placed into the reactor equipped with heating and vacuum capacity. After placing a catalyst (e.g., 0.5 g of tetramethylethylenediamine) into the reactor the reactor was sealed followed by flushing with an inert gas (e.g., nitrogen or argon) for 30 min. Next, the reactor was evacuated with a vacuum pump to a certain value (e.g. below 100 mbar). The reactor was heated to a desired temperature (>100° C.) and kept at the same temperature for 16 h. After cooling down, the silica particles were dispersed in toluene (100-mL) and sonicated for 30 min. After filtration, the cake was washed with toluene and acetone. The resulting silica was dispersed in a mixture of 5% acetic acid solution (CH$_3$CN:H$_2$O=1:1, v/v) and allowed to stand for 12 h. After filtration and being washed with acetone, the resulting silica was dried under vacuum at 105° C. for 12 h. The dried silica was placed again into the reactor equipped with heating and vacuum capacity. After placing a catalyst (e.g., 0.5 g of tetramethylethylenediamine) and 5 g of vinyldimethylethoxysilane into the reactor, the reactor was sealed followed by flushing with an inert gas (e.g., nitrogen or argon) for 30 min. Next, the reactor was evacuated with a vacuum pump to a desired value (e.g. below 100 mbar). The reactor was heated to a desired temperature (>100° C.) and kept at the same temperature for 16 h. After cooling down, the silica particles were dispersed in toluene (100-mL) and sonicated for 30 min. After filtration, the cake was washed with toluene and acetone to give to Phase 32.

Phase 33: 20 g of dried porous spherical silica particles ($d_p$, 5 µm; surface area, 200 m$^2$/g; pore size, 200 Å) were transferred into a 250-mL round bottom flask followed by the addition of a solution of 9.6 g of diethoxymethylsilyl modified poly-1,2-butadiene 5 (Gelest, Cat #SSP-058) in a suitable solvent (e.g., methanol). The resulting mixture was sonicated to uniformity and then all volatiles were completely removed under reduced pressure. The dried mixture was placed into the reactor equipped with heating and vacuum capacity. After placing a catalyst (e.g., 0.5 g of tetramethylethylenediamine) into the reactor the reactor was sealed followed by flushing with an inert gas (e.g., nitrogen or argon) for 30 min. Next, the reactor was evacuated with a vacuum pump to a certain value (e.g. below 100 mbar). The reactor was heated to a desired temperature (>100° C.) and kept at the same temperature for 16 h. After cooling down, the silica particles were dispersed in toluene (100-mL) and sonicated for 30 min. After filtration, the cake was washed with toluene and acetone. The resulting silica was dispersed in a mixture of 5% acetic acid solution (CH$_3$CN:H$_2$O=1:1, v/v) and allowed to stand for 12 h. After filtration and being washed with acetone, the resulting silica was dried under vacuum at 105° C. for 12 h. The dried silica was placed again into the reactor equipped with heating and vacuum capacity. After placing a catalyst (e.g., 0.5 g of tetramethylethylenediamine) and 5 g of vinyldimethylethoxysilane into the reactor, the reactor was sealed followed by flushing with an inert gas (e.g., nitrogen or argon) for 30 min. Next, the reactor was evacuated with a vacuum pump to a desired value (e.g. below 100 mbar). The reactor was heated to a desired temperature (>100° C.) and kept at the same temperature for 16 h. After cooling down, the silica particles were dispersed in toluene (100-mL) and sonicated for 30 min. After filtration, the cake was washed with toluene and acetone to give to Phase 33.

Phase 34: 20 g of dried porous spherical silica particles ($d_p$, 5 µm; surface area, 30 m$^2$/g; pore size, 1000 Å) were transferred into a 250-mL round bottom flask followed by the addition of a solution of 2.4 g of diethoxymethylsilyl modified poly-1,2-butadiene 5 (Gelest, Cat #SSP-058) in a suitable solvent (e.g., methanol). The resulting mixture was sonicated to uniformity and then all volatiles were completely removed under reduced pressure. The dried mixture was placed into the reactor equipped with heating and vacuum capacity. After placing a catalyst (e.g., 0.1 g of tetramethylethylenediamine) into the reactor the reactor was sealed followed by flushing with an inert gas (e.g., nitrogen or argon) for 30 min. Next, the reactor was evacuated with a vacuum pump to a certain value (e.g. below 100 mbar). The reactor was heated to a desired temperature (>100° C.) and kept at the same temperature for 16 h. After cooling down, the silica particles were dispersed in toluene (100-mL) and sonicated for 30 min. After filtration, the cake was washed with toluene and acetone. The resulting silica was dispersed in a mixture of 5% acetic acid solution (CH$_3$CN:H$_2$O=1:1, v/v) and allowed to stand for 12 h. After filtration and being washed with acetone, the resulting silica was dried under vacuum at 105° C. for 12 h. The dried silica was placed again into the reactor equipped with heating and vacuum capacity. After placing a catalyst (e.g., 0.1 g of tetramethylethylenediamine) and 1.2 g of vinyldimethylethoxysilane into the reactor, the reactor was sealed followed by flushing with an inert gas (e.g., nitrogen or argon) for 30 min. Next, the reactor was evacuated with a vacuum pump to a desired value (e.g. below 100 mbar). The reactor was heated to a desired temperature (>100° C.) and kept at the same temperature for 16 h. After cooling down, the silica particles were dispersed in toluene (100-mL) and sonicated for 30 min. After filtration, the cake was washed with toluene and acetone to give to Phase 34.

Figure 5:
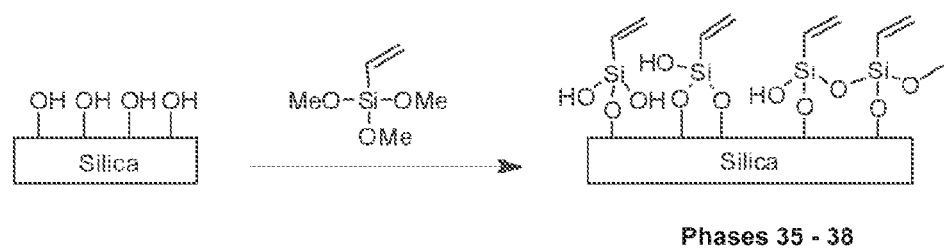
FIG. 5 (Scheme 5) shows the preparation of vinyl functionalized silica using trimethoxysilane monomer.
Figure 6:
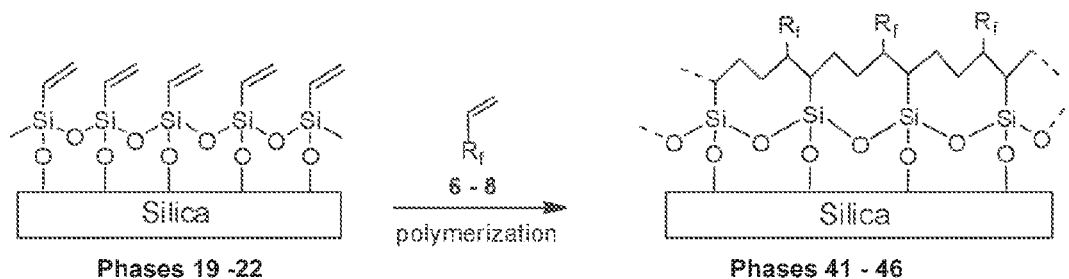
FIG. 6 (Scheme 6) shows a preparation of polymer encapsulated silica.
Figure 7:
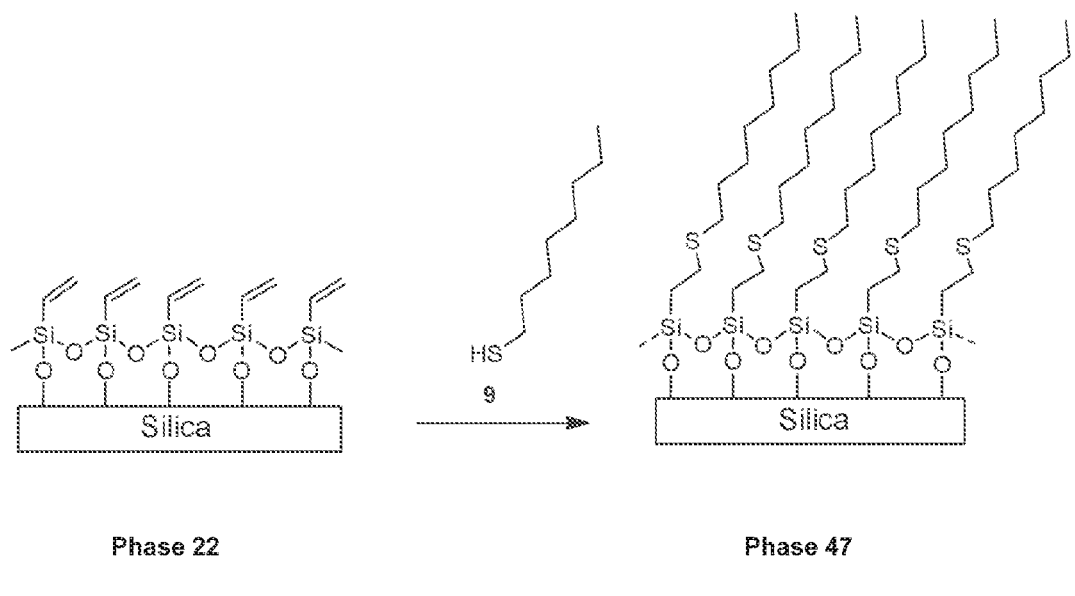
FIG. 7 (Scheme 7) shows a preparation of C8 with S linkage silica.

Example 7: Preparation of Vinyl Functionalized Silica. Preparation of Vinylalkoxysilane Monomer Modified Phase in Solvent-Free Condition at Elevated Temperature at Reduced Pressure (FIG. 5, Scheme 5)

Phase 35: 20 g of dried porous spherical silica particles ($d_p$, 5 μm; surface area, 300 m$^2$/g; pore size, 120 Å) was placed into a reactor equipped with heating and vacuum capacity. After placing a catalyst (e.g., 0.5 g of tetramethylethylenediamine) and 7 g of vinyltrimethoxysilane into the reactor, the reactor was sealed followed by flushing with an inert gas (e.g., nitrogen or argon) for 30 min. Next, the reactor was evacuated with a vacuum pump to a desired value (e.g. below 100 mbar). The reactor was heated to a desired temperature (>100° C.) and kept at the same temperature for 16 h. After cooling down, the silica particles were dispersed into toluene (100 mL) and sonicated for 30 min. After filtration the cake was washed with toluene and acetone. The resulting silica was dispersed in a mixture of 5% acetic acid solution (CH$_3$CN:H$_2$O=1:1, v/v) and allowed to stand for 12 h. After filtration, the resulting silica was dried under vacuum at 105° C. for 12 h. The dried silica was placed again into the reactor equipped with heating and vacuum capacity. After placing a catalyst (e.g., 0.5 g of tetramethylethylenediamine) and 7 g of vinyldimethylethoxysilane into the reactor, the reactor was sealed followed by flushing with an inert gas (e.g., nitrogen or argon) for 30 min. Next, the reactor was evacuated with a vacuum pump to a desired value (e.g. below 100 mbar). The reactor was heated to a desired temperature (>100° C.) and kept at the same temperature for 16 h. After cooling down, the silica particles were dispersed into toluene (100 mL) and sonicated for 30 min. After filtration the cake was washed with toluene and acetone to give to Phase 35.

Phase 36: 20 g of dried porous spherical silica particles ($d_p$, 5 μm; surface area, 225 m$^2$/g; pore size, 175 Å) was placed into a reactor equipped with heating and vacuum capacity. After placing a catalyst (e.g., 0.5 g of tetramethylethylenediamine) and 5 g of vinyltrimethoxysilane into the reactor, the reactor was sealed followed by flushing with an inert gas (e.g., nitrogen or argon) for 30 min. Next, the reactor was evacuated with a vacuum pump to a desired value (e.g. below 100 mbar). The reactor was heated to a desired temperature (>100° C.) and kept at the same temperature for 16 h. After cooling down, the silica particles were dispersed into toluene (100 mL) and sonicated for 30 min. After filtration the cake was washed with toluene and acetone. The resulting silica was dispersed in a mixture of 5% acetic acid solution (CH$_3$CN:H$_2$O=1:1, v/v) and allowed to stand for 12 h. After filtration, the resulting silica was dried under vacuum at 105° C. for 12 h. The dried silica was placed again into the reactor equipped with heating and vacuum capacity. After placing a catalyst (e.g., 0.5 g of tetramethylethylenediamine) and 5 g of vinyldimethylethoxysilane into the reactor, the reactor was sealed followed by flushing with an inert gas (e.g., nitrogen or argon) for 30 min. Next, the reactor was evacuated with a vacuum pump to a desired value (e.g. below 100 mbar). The reactor was heated to a desired temperature (>100° C.) and kept at the same temperature for 16 h. After cooling down, the silica particles were dispersed into toluene (100 mL) and sonicated for 30 min. After filtration the cake was washed with toluene and acetone to give to Phase 36.

Phase 37: 20 g of dried porous spherical silica particles ($d_p$, 5 μm; surface area, 200 m$^2$/g; pore size, 200 Å) was placed into a reactor equipped with heating and vacuum capacity. After placing a catalyst (e.g., 0.5 g of tetramethylethylenediamine) and 5 g of vinyltrimethoxysilane into the reactor, the reactor was sealed followed by flushing with an inert gas (e.g., nitrogen or argon) for 30 min. Next, the reactor was evacuated with a vacuum pump to a desired value (e.g. below 100 mbar). The reactor was heated to a desired temperature (>100° C.) and kept at the same temperature for 16 h. After cooling down, the silica particles were dispersed into toluene (100 mL) and sonicated for 30 min. After filtration the cake was washed with toluene and acetone. The resulting silica was dispersed in a mixture of 5% acetic acid solution (CH$_3$CN:H$_2$O=1:1, v/v) and allowed to stand for 12 h. After filtration, the resulting silica was dried under vacuum at 105° C. for 12 h. The dried silica was placed again into the reactor equipped with heating and vacuum capacity. After placing a catalyst (e.g., 0.5 g of tetramethylethylenediamine) and 5 g of vinyldimethylethoxysilane into the reactor, the reactor was sealed followed by flushing with an inert gas (e.g., nitrogen or argon) for 30 min. Next, the reactor was evacuated with a vacuum pump to a desired value (e.g. below 100 mbar). The reactor was heated to a desired temperature (>100° C.) and kept at the same temperature for 16 h. After cooling down, the silica particles were dispersed into toluene (100 mL) and sonicated for 30 min. After filtration the cake was washed with toluene and acetone to give to Phase 37.

Phase 38: 20 g of dried porous spherical silica particles ($d_p$, 5 μm; surface area, 30 m$^2$/g; pore size, 1000 Å) was placed into a reactor equipped with heating and vacuum capacity. After placing a catalyst (e.g., 0.15 g of tetramethylethylenediamine) and 1 g of vinyltrimethoxysilane into the reactor, the reactor was sealed followed by flushing with an inert gas (e.g., nitrogen or argon) for 30 min. Next, the reactor was evacuated with a vacuum pump to a desired value (e.g. below 100 mbar). The reactor was heated to a desired temperature (>100° C.) and kept at the same temperature for 16 h. After cooling down, the silica particles were dispersed into toluene (100 mL) and sonicated for 30 min. After filtration the cake was washed with toluene and acetone. The resulting silica was dispersed in a mixture of 5% acetic acid solution (CH$_3$CN:H$_2$O=1:1, v/v) and allowed to stand for 12 h. After filtration, the resulting silica was dried under vacuum at 105° C. for 12 h. The dried silica was placed again into the reactor equipped with heating and vacuum capacity. After placing a catalyst (e.g., 0.15 g of tetramethylethylenediamine) and 1 g of vinyldimethylethoxysilane into the reactor, the reactor was sealed followed by flushing with an inert gas (e.g., nitrogen or argon) for 30 min. Next, the reactor was evacuated with a vacuum pump to a desired value (e.g. below 100 mbar). The reactor was heated to a desired temperature (>100° C.) and kept at the same temperature for 16 h. After cooling down, the silica particles were dispersed into toluene (100 mL) and sonicated for 30 min. After filtration the cake was washed with toluene and acetone to give to Phase 38.

Example 8: Preparation of Polymer Encapsulated Silica Phases Using Free Radical Polymerization (Schemes 6, 7)

Phase 41: 15 mL of a solvent (e.g., dichloromethane) was added to 5 g of vinyl-functionalized silica (Phase 19), 3 g of 1-octadecene 6 (e.g., Aldrich) and 0.8 g of dicumyl peroxide (e.g.: Aldrich). The resulting mixture was sonicated until uniformity and then all volatiles were removed at reduced pressure with a rotary evaporator. Next, the resulting mixture was transferred into a 100-mL glass bottle with a screw cap fitted with both gas inlet and outlet. After purging the bottle with an inert gas (e.g., nitrogen or argon) for 15 min, the bottle was sealed (at 1 atm pressure) and heated to a desired temperature (50-300° C.). After being kept at the same temperature for 16 h, the reaction was cooled down, and the reaction mixture was dispersed in toluene and sonicated for 30 min. After filtration, the cake was thoroughly washed with toluene and acetone to give Phase 41.

Phase 42: 15 mL of a solvent (e.g., dichloromethane) was added 5 g of vinyl-functionalized silica (Phase 20), 2.5 g of 1-octadecene 6 (e.g., Aldrich) and 0.5 g of dicumyl peroxide (e.g.: Aldrich). The resulting mixture was sonicated until uniformity and then all volatiles were removed at reduced pressure with a rotary evaporator. Next, the resulting mixture was transferred into a 100-mL glass bottle with a screw cap fitted with both gas inlet and outlet. After purging the bottle with an inert gas (e.g., nitrogen or argon) for 15 min, the bottle was sealed and heated to a desired temperature (50-300° C.). After being kept at the same temperature for 16 h, the reaction was cooled down, and the reaction mixture was dispersed in toluene and sonicated for 30 min. After filtration, the cake was thoroughly washed with toluene and acetone to give Phase 42.

Phase 43: 15 mL of a solvent (e.g., dichloromethane) was added 5 g of vinyl-functionalized silica (Phase 21), 2.5 g of 1-octadecene 6 (e.g., Aldrich) and 0.5 g of dicumyl peroxide (e.g.: Aldrich). The resulting mixture was sonicated until uniformity and then all volatiles were removed at reduced pressure with a rotary evaporator. Next, the resulting mixture was transferred into a 100-mL glass bottle with a screw cap fitted with both gas inlet and outlet. After purging the bottle with an inert gas (e.g., nitrogen or argon) for 15 min, the bottle was sealed and heated to a desired temperature (50-300° C.). After being kept at the same temperature for 16 h, the reaction was cooled down, and the reaction mixture was dispersed in toluene and sonicated for 30 min. After filtration, the cake was thoroughly washed with toluene and acetone to give Phase 43.

Phase 44: 15 mL of a solvent (e.g., dichloromethane) was added 5 g of vinyl-functionalized silica (Phase 22), 1 g of 1-octadecene 6 (e.g., Aldrich) and 0.35 g of dicumyl peroxide (e.g.: Aldrich). The resulting mixture was sonicated until uniformity and then all volatiles were removed at reduced pressure with a rotary evaporator. Next, the resulting mixture was transferred into a 100-mL glass bottle with a screw cap fitted with both gas inlet and outlet. After purging the bottle with an inert gas (e.g., nitrogen or argon) for 15 min, the bottle was sealed and heated to a desired temperature (50-300° C.). After being kept at the same temperature for 16 h, the reaction was cooled down, and the reaction mixture was dispersed in toluene and sonicated for 30 min. After filtration, the cake was thoroughly washed with toluene and acetone to give Phase 44.

Phase 45: 15 mL of a solvent (e.g., dichloromethane) was added 5 g of vinyl-functionalized silica (Phase 22), 0.3 g of 1-octene 7 (e.g., Aldrich) and 0.35 g of dicumyl peroxide (e.g.: Aldrich). The resulting mixture was sonicated until uniformity and then all volatiles were removed at reduced pressure with a rotary evaporator. Next, the resulting mixture was transferred into a 100-mL glass bottle with a screw cap fitted with both gas inlet and outlet. After purging the bottle with an inert gas (e.g., nitrogen or argon) for 15 min, the bottle was sealed and heated to a desired temperature (50-300° C.). After being kept at the same temperature for 16 h, the reaction was cooled down, and the reaction mixture was dispersed in toluene and sonicated for 30 min. After filtration, the cake was thoroughly washed with toluene and acetone to give Phase 45.

Phase 46: 15 mL of a solvent (e.g., dichloromethane) was added 5 g of vinyl-functionalized silica (Phase 22), 0.56 g of allylbenzene 8 (e.g., Aldrich) and 0.35 g of dicumyl peroxide (e.g.: Aldrich). The resulting mixture was sonicated until uniformity and then all volatiles were removed at reduced pressure with a rotary evaporator. Next, the resulting mixture was transferred into a 100-mL glass bottle with a screw cap fitted with both gas inlet and outlet. After purging the bottle with an inert gas (e.g., nitrogen or argon) for 15 min, the bottle was sealed and heated to a desired temperature (50-300° C.). After being kept at the same temperature for 16 h, the reaction was cooled down, and the reaction mixture was dispersed in toluene and sonicated for 30 min. After filtration, the cake was thoroughly washed with toluene and acetone to give Phase 46.

Preparation of C8 with S Linkage Silica Phase:

Phase 47: 15 mL of a solvent (e.g., dichloromethane) was added 5 g of vinyl-functionalized silica (Phase 22), 0.53 g of 1-octanethiol 9 (e.g., Aldrich) and 0.35 g of dicumyl peroxide (e.g.: Aldrich). The resulting mixture was sonicated until uniformity and then all volatiles were removed at reduced pressure with a rotary evaporator. Next, the resulting mixture was transferred into a 100-mL glass bottle with a screw cap fitted with both gas inlet and outlet. After purging the bottle with an inert gas (e.g., nitrogen or argon) for 15 min, the bottle was sealed and heated to a desired temperature (50-300° C.). After being kept at the same temperature for 16 h, the reaction was cooled down, and the reaction mixture was dispersed in toluene and sonicated for 30 min. After filtration, the cake was thoroughly washed with toluene and acetone to give Phase 47.

The summary of phases prepared and reaction conditions are shown in Tables 2 and 3:

TABLE 2

Preparation of a variety of vinyl silica phases with different polymer/monomer starting materials (reaction schemes 1-5):

| Vinyl functionalized Phase | Bonding condition | Silica substrate ($d_p$/pore size/ surface area) | Polymer/ Monomer |
|---|---|---|---|
| Phase 10 | Toluene/reflux | 3 μm/175 Å/ 225 m²/g | 1 or 2 |
| Phase 11 | Toluene/reflux | 5 μm/120 Å/ 300 m²/g | 1 or 2 |
| Phase 12 | Toluene/reflux | 5 μm/175 Å/ 225 m²/g | 1 or 2 |
| Phase 13 | Toluene/reflux | 5 μm/200 Å/ 200 m²/g | 1 or 2 |
| Phase 14 | Toluene/reflux | 5 μm/1000 Å/ 30 m²/g | 1 or 2 |
| Phase 15 | 160° C., solvent free, 1 atm | 5 μm/120 Å/ 300 m²/g | 1 or 2 |

TABLE 2-continued

Preparation of a variety of vinyl silica phases with different polymer/monomer starting materials (reaction schemes 1-5):

| Vinyl functionalized Phase | Bonding condition | Silica substrate ($d_p$/pore size/ surface area) | Polymer/ Monomer |
|---|---|---|---|
| Phase 16 | 160° C., solvent free, 1 atm | 5 μm/175 Å/ 225 m²/g | 1 or 2 |
| Phase 17 | 160° C., solvent free, 1 atm | 5 μm/200 Å/ 200 m²/g | 1 or 2 |
| Phase 18 | 160° C., solvent free, 1 atm | 5 μm/1000 Å/ 30 m²/g | 1 or 2 |
| Phase 19 | >150° C., solvent free, reduced pressure | 5 μm/120 Å/ 300 m²/g | 1 or 2 |
| Phase 20 | >150° C., solvent free, reduced pressure | 5 μm/175 Å/ 225 m²/g | 1 or 2 |
| Phase 21 | >150° C., solvent free, Reduced pressure | 5 μm/200 Å/ 200 m²/g | 1 or 2 |
| Phase 22 | >150° C., solvent free, reduced pressure | 5 μm/1000 Å/ 30 m²/g | 1 or 2 |
| Phase 23 | >150° C., solvent free, reduced pressure | 5 μm/120 Å/ 300 m²/g | 3 |
| Phase 24 | >150° C., solvent free, reduced pressure | 5 μm/175 Å/ 225 m²/g | 3 |
| Phase 25 | >150° C., solvent free, reduced pressure | 5 μm/200 Å/ 200 m²/g | 3 |
| Phase 26 | >150° C., solvent free, reduced pressure | 5 μm/1000 Å/ 30 m²/g | 3 |
| Phase 27 | >150° C., solvent free, reduced pressure | 5 μm/120 Å/ 300 m²/g | 4 |
| Phase 28 | >150° C., solvent free, reduced pressure | 5 μm/175 Å/ 225 m²/g | 4 |
| Phase 29 | >150° C., solvent free, reduced pressure | 5 μm/200 Å/ 200 m²/g | 4 |
| Phase 30 | >150° C., solvent free, reduced pressure | 5 μm/1000 Å/ 30 m²/g | 4 |
| Phase 31 | >150° C., solvent free, reduced pressure | 5 μm/120 Å/ 300 m²/g | 5 |
| Phase 32 | >150° C., solvent free, reduced pressure | 5 μm/175 Å/ 225 m²/g | 5 |
| Phase 33 | >150° C., solvent free, reduced pressure | 5 μm/200 Å/ 200 m²/g | 5 |
| Phase 34 | >150° C., solvent free, reduced pressure | 5 μm/1000 Å/ 30 m²/g | 5 |
| Phase 35 | >150° C., solvent free, reduced pressure | 5 μm/120 Å/ 300 m²/g | Vinyltrimethoxy silane |
| Phase 36 | >150° C., solvent free, reduced pressure | 5 μm/175 Å/ 225 m²/g | Vinyltrimethoxy silane |
| Phase 37 | >150° C., solvent free, reduced pressure | 5 μm/200 Å/ 200 m²/g | Vinyltrimethoxy silane |
| Phase 38 | >150° C., solvent free, reduced pressure | 5 μm/1000 Å/ 30 m²/g | Vinyltrimethoxy silane |

TABLE 3

Preparation of polymer encapsulated silica (PES) phases (reaction schemes 6-7).

| PES Phase | $(CH_2=CH)R_f$ | Polymerization condition | Vinyl functionalized Phase |
|---|---|---|---|
| Phase 41 | $CH_2=CHC_{16}H_{33}$ 6 | Dicumyl peroxide, >120° C. | Phase 19 |
| Phase 42 | $CH_2=CHC_{16}H_{33}$ 6 | Dicumyl peroxide, >120° C. | Phase 20 |
| Phase 43 | $CH_2=CHC_{16}H_{33}$ 6 | Dicumyl peroxide, >120° C. | Phase 21 |
| Phase 44 | $CH_2=CHC_{16}H_{33}$ 6 | Dicumyl peroxide, >120° C. | Phase 22 |
| Phase 45 | $CH_2=CHC_6H_{13}$ 7 | Dicumyl peroxide, >120° C. | Phase 22 |
| Phase 46 | $CH2=CHCH_2Ph$ 8 | Dicumyl peroxide, >120° C. | Phase 22 |
| Phase 47 | $C_8H_{17}SH$ 9 | Dicumyl peroxide, >120° C. | Phase 22 |

Example 9: Low pH Stability

The test consisted of repeated cycles of acid stress conditions and column testing.

The performance test condition: stationary phase, Phase 42 and a commercial C18; column dimension: 3×150 mm; mobile phase: 10% acetonitrile/90% 10 mM ammonium acetate (pH=5.2); flow rate, 0.425 mL/min; injection volume, 2 μL; temperature, 30° C.; detection, UV at 220 nm; test probes, uracil (0.15 mg/mL), acetanilide (2 mg/mL).

The acid stress condition: mobile phase, 0.1 M TFA; flow rate, 0.425 mL/min; temperature, 80° C.; duration time, 3 h.

Figure 8:
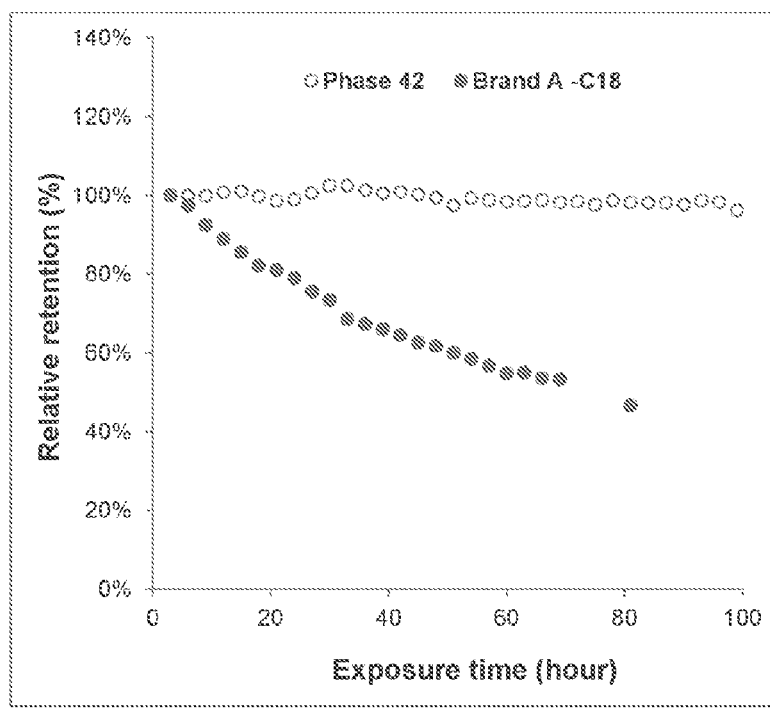
FIG. 8 illustrates a hydrolytic stability test at pH 1 (0.1M TFA) and 80° C. using newly developed pH stable C18 phase 42 and well-known C18 column (brand A).

FIG. 8 illustrates the hydrolytic stability test of Phase 42 (open circles) compared to a commercial C18 phase (filled circles) made from conventional C18 silane chemistry (e.g., non-polymeric silane chemistry) under low pH condition (0.1 M TFA, pH ~1). During the test period of 100 h, the retention time of acetanilide peak changed ~4% for Phase 42. For the commercial C18 phase, it decreased larger than 50% after 80 h acid treatment. Phase 42 shows superior hydrolytic stability at low pH condition.

Example 10: High pH Stability

The test consisted of repeated cycles of base stress conditions and column testing. The performance test condition was: column, packing Phase 43, dimension, 3×150 mm; mobile phase, 10% acetonitrile/90% 10 mM ammonium acetate (pH=5.2); flow rate, 0.425 mL/min; injection volume, 2 μL; temperature, 30° C.; detection, UV at 220 nm; test probes, uracil (0.15 mg/mL), procainamide (0.15 mg/mL), sodium tosylate (0.15 mg/mL), acetanilide (2 mg/mL).

The base stress condition was: mobile phase, 0.1 M NaOH in 10% methanol; temperature, 30° C.; duration time, 1 h.

Figure 9:
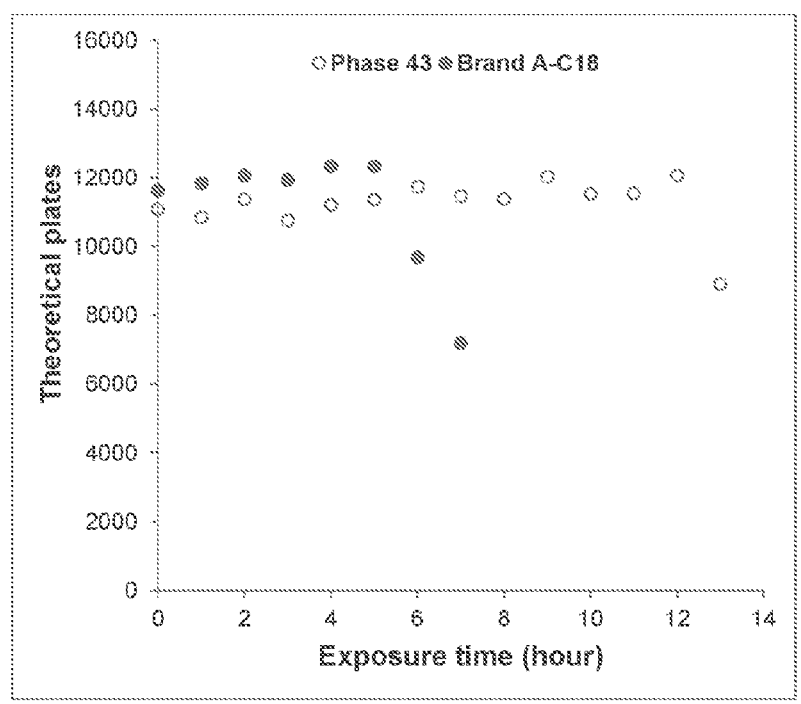
FIG. 9 illustrates a hydrolytic stability test at pH 13 (0.1M NaOH) and 30° C. using newly developed pH stable C18 phase 43 and well-known C18 column (brand A).

FIG. 9 illustrates the hydrolytic stability test of Phase 43 (open circles) compared to Brand A-C18 phase (filled circles) under high pH condition (0.1 M NaOH, pH 13). The efficiency of acetanilide peak started to decrease dramatically after 12 h base treatment for Phase 43. However, it occurred after 5 hours treatment for the Brand A-C18 phase. Phase 43 has better high pH stability than the Brand A-C18 phase.

Example 11: Performance Test

In order to evaluate the column performance packed with Phase 42, a mixture containing uracil, dimethylphthalate, and phenanthrene was used to perform the chromatographic separation.

The test conditions were: column, packing Phase 42, particle size 5 μm, column dimension: 3×150 mm; mobile phase: acetonitrile/D.I. water (70/30, v/v); flow rate, 0.425 mL/min; injection volume: 2 μL; temperature, 30° C.; detection, UV at 220 nm; and test probes: uracil (peak 1, 0.15 mg/mL), dimethylphthalate (peak 2, 0.75 mg/mL), and phenanthrene (peak 3, 0.15 mg/mL).

Figure 10:
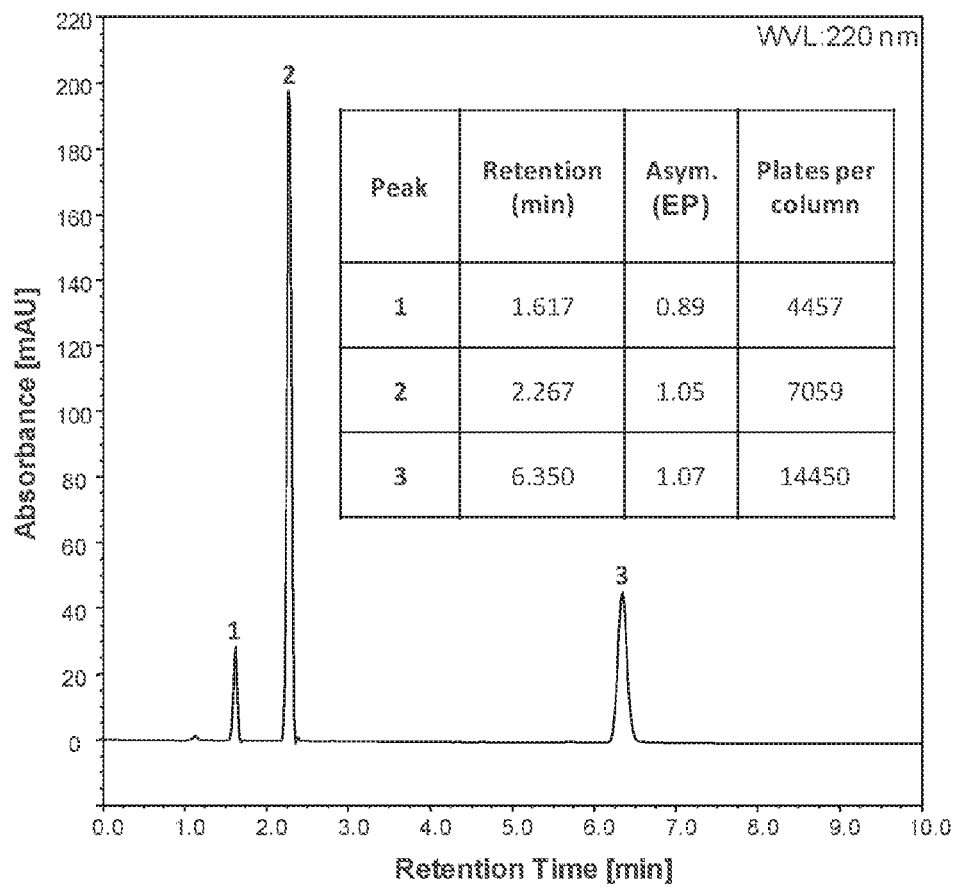
FIG. 10 shows the performance test of a column packed with the newly developed pH stable C18 phase 42.

FIG. 10 illustrates the chromatographic performance of column packed with Phase 42, including hydrophobic retention, peak asymmetry and efficiency.

Example 12: Aminoglycoside Separations

A series of aminoglycoside antibiotics (e.g., gentamicin, spectinomycin, kanamycin, ribostamycin, streptomycin, apramycin, paromomycin, dihydrostreptomycin, neomycin, netilmycin, tobramycin, amikacin, arbekacin) were analyzed by the column packed with Phase 42 using ion-pairing reserved-phase liquid chromatography (RPLC) because they are highly hydrophilic and difficult to retain on the conventional reversed-phase column. Trifluoroacetic acid (TFA) and heptafluorobutyric acid (HFBA) were used as the ion-pairing reagents to help retain aminoglycosides. 100 mM TFA in DI water with around pH 1 was mainly used as the mobile phase. Small amount of HFBA was added in the mobile phase to increase retention and adjust the selectivity.

Figure 11:
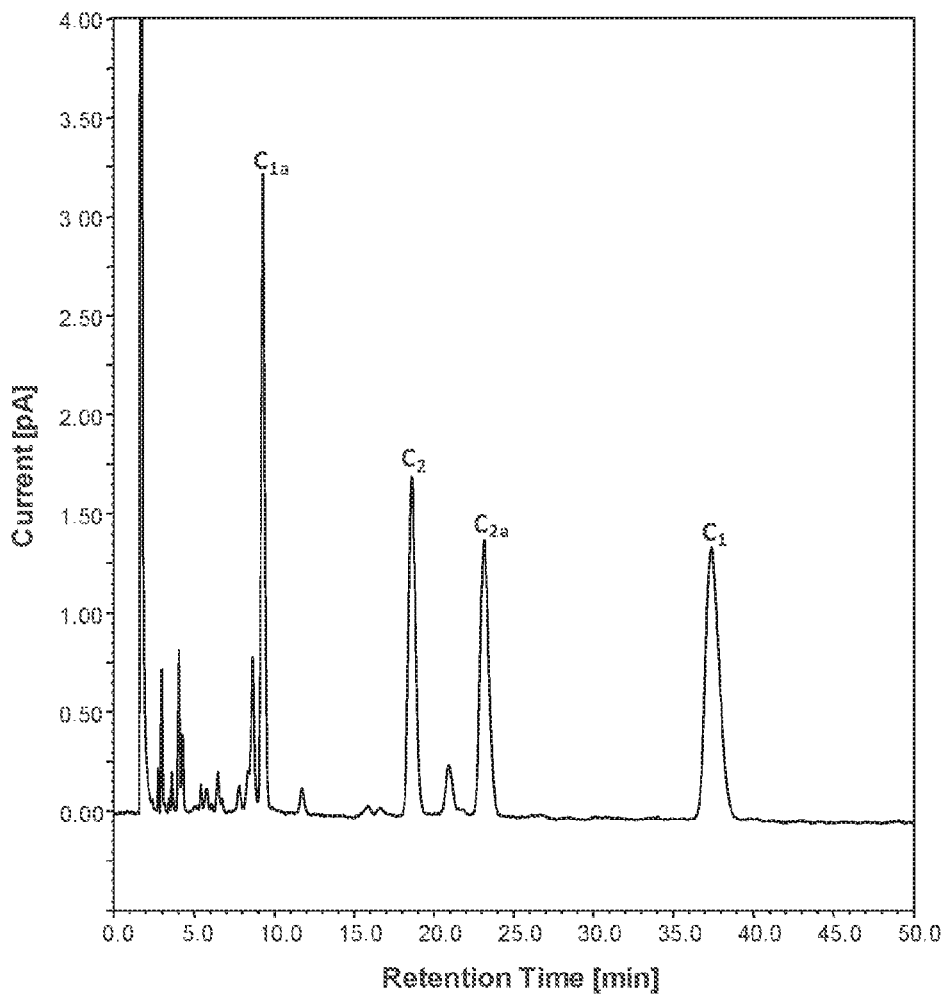
FIG. 11 shows the ion-pairing reversed phase LC separation of gentamicin sulfate at the low pH condition (100 mM TFA, pH ~1) using the newly developed C18 phase 42.

FIG. 11 illustrates the HPLC separation of gentamicin sulfate. Four major components of gentamicin ($C_1$, $C_{1a}$, $C_2$, and $C_{2a}$) were totally separated. More than 15 gentamicin related substances and impurities were observed as the minor peaks. The test conditions were: column, packing Phase 42, particle size 5 μm, column dimension: 3×150 mm; mobile phase: 100 mM TFA; flow rate, 0.425 mL/min; injection volume: 2 μL; temperature, 30° C.; detection, corona aerosol detector; and test sample: gentamicin sulfate (1 mg/mL).

Figure 12:
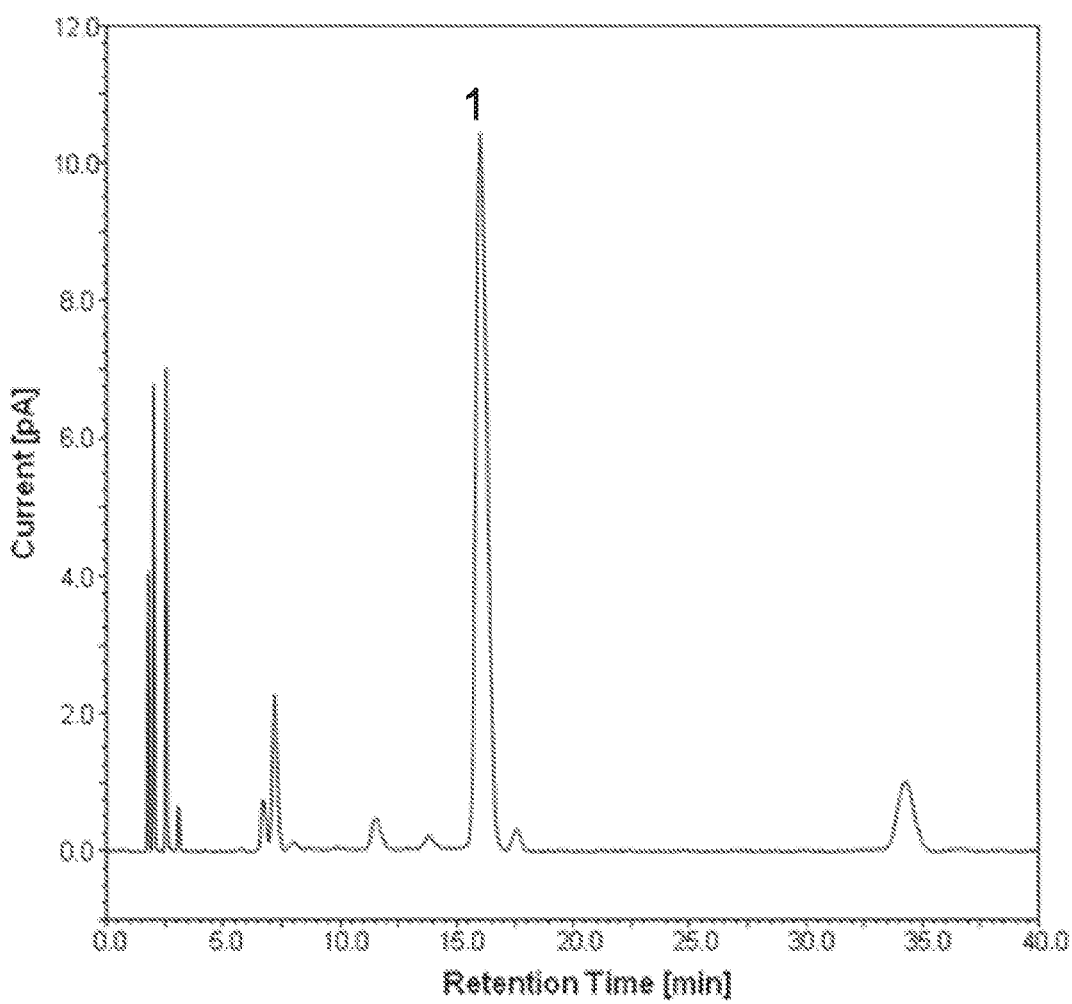
FIG. 12 shows the ion-pair reversed phase LC separation of spectinomycin sulfate at the low pH condition and in the presence of HFBA using the newly developed C18 phase 42.

FIG. 12 illustrates the HPLC separation of spectinomycin sulfate (shown as peak 1). HFBA was used to obtain optimal separation. The test conditions were: column, packing Phase 42, particle size 5 μm, column dimension: 3×150 mm; mobile phase: 100 mM TFA/100 mM HFBA (93/7, v/v); flow rate, 0.425 mL/min; injection volume: 5 μL; temperature, 30° C.; detection, corona aerosol detector; and test sample: spectinomycin sulfate (1 mg/mL).

Figure 13:
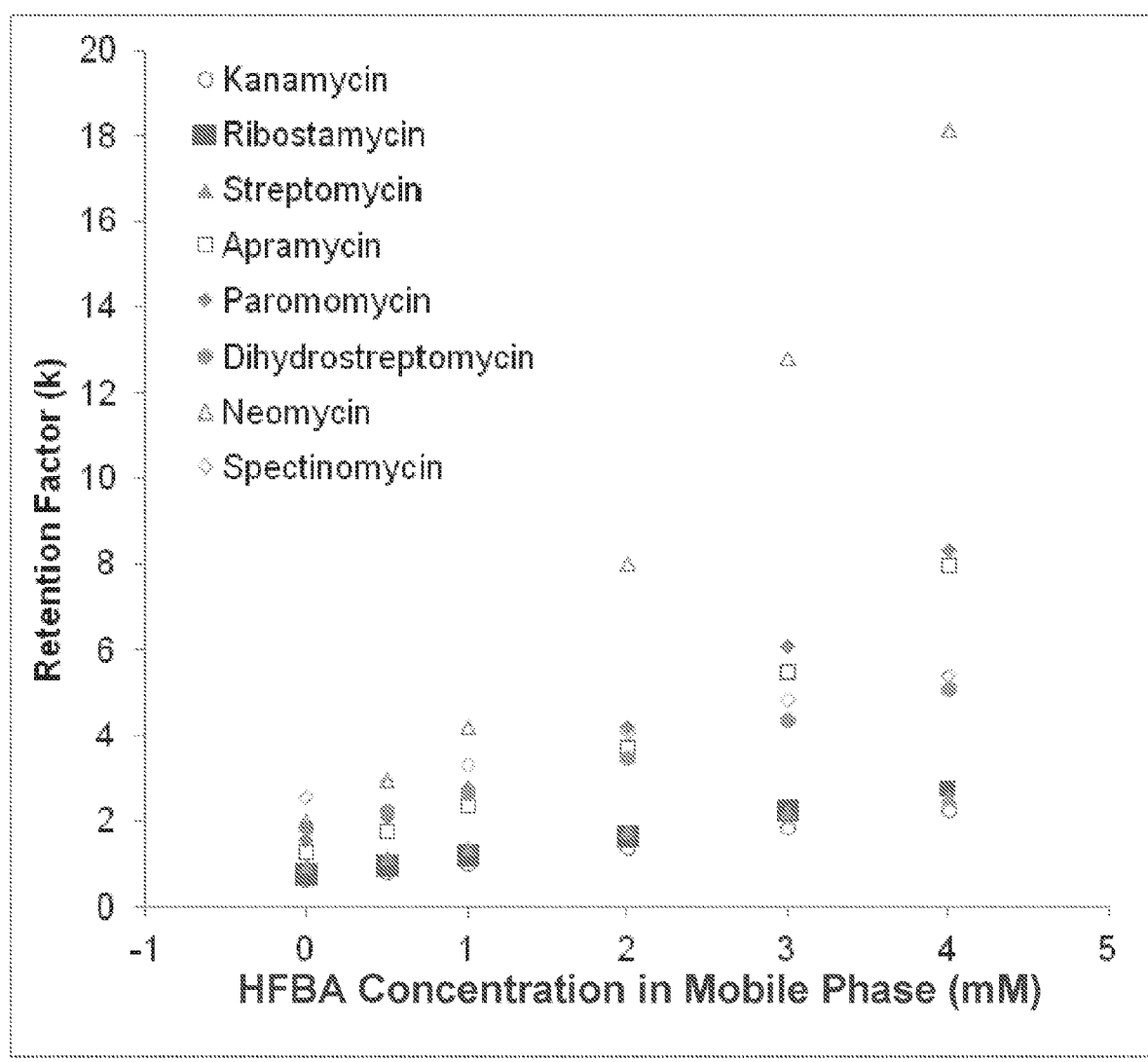
FIG. 13 illustrates the effect of HFBA concentration in the mobile phase (100 mM TFA) on the retention factors of 8 aminoglycoside antibiotics when using the newly developed C18 phase 42.

FIG. 13 illustrates the variation of retention factor (k) for different aminoglycosides with the addition of HFBA in 100 mM TFA mobile phase. With increasing HFBA concentrations, the retention factors of all aminoglycosides increased because HFBA is a much stronger ion-pairing reagent. However, the increase was at different degrees for the various aminoglycosides. In general, for the aminoglycoside containing more amino groups, the k values increased more with increasing HFBA content in the mobile phase compared to aminoglycoside containing relatively fewer amino groups. For example, neomycin contains 6 primary amino groups and its k value increased 9 times after addition of 4 mM HFBA. Spectinomycin has two secondary amino groups and its k value only increased about 2 times under the same conditions. Therefore, the selectivity for the aminoglycoside antibiotics can be adjusted by addition of HFBA in the mobile phase (100 mM TFA). The test conditions were: column, packing Phase 42, particle size 5 μm, column dimension: 3×150 mm; mobile phase: various concentrations of HFBA (0.0.5 mM, 1 mM, 2 mM, 3 mM, and 4 mM) in 100 mM TFA; flow rate, 0.425 mL/min; injection volume: 2 μL; temperature, 30° C.; detection, corona aerosol detector; and test samples: kanamycin sulfate (1 mg/mL), ribostamycin sulfate (1 mg/mL), streptomycin sulfate (1 mg/mL), apramycin sulfate (1 mg/mL), paromomycin sulfate (1 mg/mL), dihydrostreptomycin sulfate (1 mg/mL), neomycin sulfate (1 mg/mL), and spectinomycin sulfate (1 mg/mL).

Example 13: Ruggedness for Aminoglycosides

Figure 14:
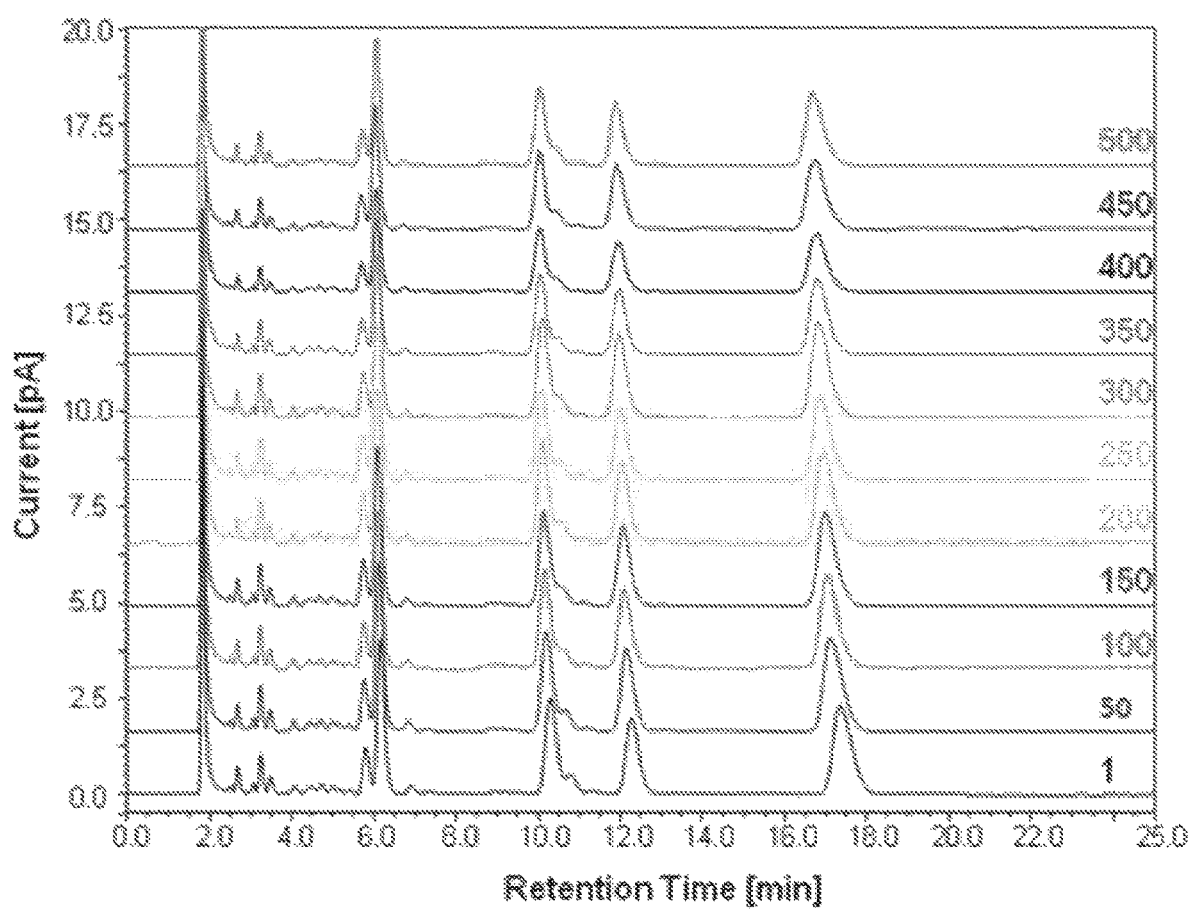
FIG. 14 illustrates the ruggedness test of the column packed with the newly developed C18 phase 42 under low pH condition (100 mM TFA, pH ~1) and 50° C. using gentamicin as the testing probe.

In order to evaluate the ruggedness for the challenging chromatographic condition required for aminoglycoside antibiotics, a column packed with Phase 42 was subjected to more than 500 consecutive runs for gentamycin separation at 50° C. using 100 mM TFA (about pH 1) as the mobile phase. FIG. 14 illustrates the overlay of separations during the process. Overall, Phase 42 exhibited exceptional chemical and chromatographic stability during the study—merely less than 4% retention loss was observed compared to greater than 50% retention loss for a commercial C18 phase made from the conventional silane chemistry.

The test conditions were: column, packing Phase 42, particle size 5 μm, column dimension: 3×150 mm; mobile phase: 100 mM TFA; flow rate, 0.425 mL/min; injection volume: 2 μL; temperature, 50° C.; detection, corona aerosol detector (CAD, commercially available from Thermo Fisher Scientific); and test sample: gentamicin sulfate (1 mg/mL).

In view of the foregoing, the invention may be provided in accordance with any of the following numbered clauses:

(1) A chromatographic material comprising:
a substrate having a surface and the substrate having a polymeric layer covalently bound to the surface;
the polymeric layer comprising polymer molecules covalently attached to the surface of the substrate, each polymer molecule being attached to the surface via multiple siloxane bonds and each polymer molecule being connected to one or more functionalizing compounds that each comprise a functional group.

(2) The chromatographic material according to clause 1, wherein the polymeric layer is formed by covalently attaching polymer molecules to the surface of the substrate via multiple siloxane bonds, each polymer molecule containing multiple first reactive groups, and reacting the first reactive groups of the attached polymer molecules with at least one functionalizing compound that comprises a second reactive group that is reactive with the first reactive groups and that further comprises a functional group.

(3) The chromatographic material according to any preceding clause, wherein the functional group has chromatographic functionality and is selected from the group consisting of alkyl and aryl.

(4) The chromatographic material according to any preceding clause, wherein the first reactive groups comprise olefinic groups.

(5) The chromatographic material according to any preceding clause, wherein the first reactive groups comprise a member selected from the group consisting of vinyl groups and allyl groups.

(6) The chromatographic material according to any preceding clause, wherein all of the first reactive groups are vinyl groups.

(7) The chromatographic material according to any preceding clause, wherein there is a substantially uniform distance between adjacent first reactive groups of the polymer.

(8) The chromatographic material according to any preceding clause, wherein the second reactive group comprises a member selected from the group consisting of an olefinic group and a thiol group.

(9) The chromatographic material according to any preceding clause, wherein the second reactive group comprises a member selected from the group consisting of a vinyl group and an allyl group.

(10) The chromatographic material according to any preceding clause, wherein the polymer molecule is based on a vinylsiloxane.

(11) The chromatographic material according to any preceding clause, wherein the vinylsiloxane polymer has a formula I:

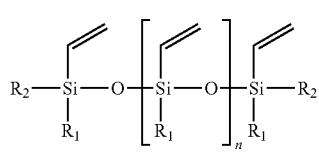

Formula I wherein n is an integer from 3 to 100, $R_1$ and $R_2$ are independently selected from the group consisting of: alkoxy, hydroxyl and halo.

(12) The chromatographic material according to clause 11, wherein $R_1$ and $R_2$ are independently selected from the group consisting of: methoxy, ethoxy and hydroxyl.

(13) The chromatographic material according to clause 10, wherein the vinylsiloxane polymer is a co-polymer.

(14) The chromatographic material according to clause 10 or 13, wherein the vinylsiloxane co-polymer has a formula III:

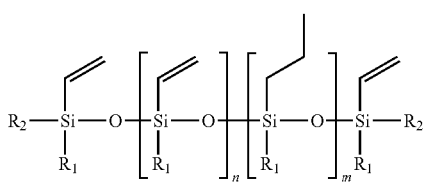

Formula III wherein $R_1$ and $R_2$ are independently selected from the group consisting of: alkoxy, hydroxyl and halo; and wherein n is an integer from 3 to 100, and m is an integer from 1 to 70.

(15) The chromatographic material according to any preceding clause, wherein the polymer molecule is a silyl modified polybutadiene.

(16) The chromatographic material according to clause 15, wherein the silyl modified polybutadiene is an alkoxysilyl modified polybutadiene having a repeat unit of formula VI:

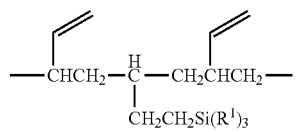

Formula VI wherein each $R^1$ is independently selected from the group consisting of: methoxy and ethoxy.

(17) The chromatographic material according to clause 15 or 16, wherein the silyl modified polybutadiene is an alkylalkoxysilyl modified polybutadiene.

(18) A method of forming functionalized silica for chromatographic use, the method comprising:

in a first stage, reacting silica with at least one first functionalizing compound under conditions of at least about 100° C. and of less than 500 mbar, the first functionalizing compound or compounds comprising:

one or more silyl groups for reacting with the surface of the silica; and one or more first reactive groups, thereby covalently attaching the first functionalizing compound or compounds to the surface of the silica and leaving the first reactive groups unreacted; and in a second stage, reacting the one or more first reactive groups of the surface bound first functionalizing compound or compounds with at least one second functionalizing compound, the second functionalizing compound comprises:

one or more second reactive groups reactive with the one or more first reactive groups; and a functional group.

(19) The method according to clause 18, wherein the first functionalizing compound is a polymer.

(20) The method according to any of clauses 18 to 19, wherein the polymer is selected from the group consisting of: siloxane polymer; vinylsiloxane polymer; vinylalkoxysiloxane; silyl modified polybutadiene; and alkoxysilyl modified polybutadiene.

(21) The method according to any of clauses 18 to 20, wherein the first reactive groups are selected from the group consisting of vinyl and allyl groups.

(22) The method according to any of clauses 18 to 21, wherein the second functionalizing compound comprises a C4-C30 alkene.

(23) The method according to any of clauses 18 to 22, wherein the one or more second reactive groups are selected from the group consisting of olefinic groups and thiol groups.

(24) The method according to any of clauses 18 to 23, wherein the temperature in the first stage when reacting silica with at least one first functionalizing compound is at least about 200° C.

(25) The method according to any of clauses 18 to 24, wherein the temperature in the first stage when reacting silica with at least one first functionalizing compound is in the range about 200 to about 300° C.

(26) The method according to any of clauses 18 to 25, wherein the pressure in the first stage when reacting silica with at least one first functionalizing compound is less than 100 mbar.

(27) The method according to any of clauses 18 to 26, wherein the pressure in the first stage when reacting silica with at least one first functionalizing compound is from about 0.1 mbar to about 100 mbar.

(28) The method according to any of clauses 18 to 27, wherein reacting silica with at least one first functionalizing compound in the first stage is performed in the absence of a solvent.

(29) The method according to any of clauses 18 to 28, wherein reacting silica with at least one first functionalizing compound in the first stage is performed in the presence of a catalyst.

(30) The method according to any of clauses 18 to 29, wherein the temperature in the second stage when reacting the one or more first reactive groups with the second functionalizing compound is at least about 100° C.

(31) The method according to any of clauses 18 to 30, wherein the temperature in the second stage when reacting the one or more first reactive groups with the second functionalizing compound is in the range from about 100 to about 200° C.

(32) The method according to any of clauses 18 to 31, wherein the pressure in the second stage when reacting the one or more first reactive groups with the second functionalizing compound is at least atmospheric pressure.

(33) The method according to any of clauses 18 to 32, wherein the pressure in the second stage when reacting the one or more first reactive groups with the second functionalizing compound is less than 500 mbar.

(34) A method of forming functionalized silica for chromatographic use, the method comprising:
in a first stage, reacting silica with at least one first functionalizing compound under conditions of at least about 100° C., the first functionalizing compound or compounds comprising
a polymer or polymers having multiple silyl groups for reacting with the surface of the silica and
multiple first reactive groups,
thereby covalently attaching the first functionalizing compound or compounds to the surface of the silica and leaving the first reactive groups unreacted; and
in a second stage, reacting the one or more first reactive groups of the surface bound first functionalizing compound or compounds with at least one second functionalizing compound, the second functionalizing compound comprises:
one or more second reactive groups reactive with the one or more first reactive groups; and
a functional group.

(35) A method of separating aminoglycoside antibiotics comprising flowing a mobile phase containing a sample comprising one or more aminoglycoside antibiotics through a column to chromatographically separate the one or more aminoglycoside antibiotics from each other, wherein the column is packed with the chromatographic material according to any of clauses 1 to 17.

(36) The method according to clause 35, wherein the pH of the mobile phase is 1.0 or less or 13.0 or higher.

(37) A chromatographic material made by a process, the process comprising:
in a first stage, reacting silica with at least one first functionalizing compound under conditions of at least about 100° C. and of less than 500 mbar, the first functionalizing compound or compounds comprising:
one or more silyl groups for reacting with the surface of the silica; and one or more first reactive groups,
thereby covalently attaching the first functionalizing compound or compounds to the surface of the silica and leaving the first reactive groups unreacted; and
in a second stage, reacting the one or more first reactive groups of the surface bound first functionalizing compound or compounds with at least one second functionalizing compound, the second functionalizing compound comprises:
one or more second reactive groups reactive with the one or more first reactive groups; and
a functional group;
whereby a retention time of a chromatographic analysis of a hydrophobic neutral compound does not vary by more than +/−10% while a mobile phase is flowed through the chromatographic material for more than 20 hours, where the mobile phase has a pH of about 1 or less.

(38) The chromatographic material of clause 37, the process further comprising:
repeating a step of reacting the silica with the at least one first functionalizing compound under conditions of at least about 100° C. and of less than 500 mbar during the first stage, but before the second stage; and
repeating a step of reacting the one or more first reactive groups of the surface bound first functionalizing compound or compounds with the at least one second functionalizing compound under conditions of at least about 100° C. and of less than 500 mbar during the second stage.

(39) The chromatographic material of clause 37 or 38, wherein the reacting of silica with at least one first functionalizing compound in the first stage is performed in the absence of a solvent.

(40) The chromatographic material of any of clauses 37 to 39, wherein reacting the one or more first reactive groups of the surface bound first functionalizing compound or compounds with the at least one second functionalizing compound in the second stage is performed in the absence of a solvent.

(41) The chromatographic material of any of clauses 37 to 40, wherein reacting silica with at least one first functionalizing compound in the first stage is performed in the presence of a catalyst.

(42) The chromatographic material of any of clauses 37 to 41, wherein the first functionalizing compound comprises a vinylsiloxane polymer.

(43) The chromatographic material of any of clauses 37 to 42, wherein the vinylsiloxane polymer has a formula I:

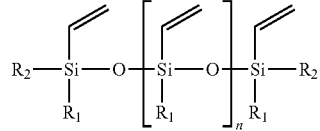

Formula I wherein n is an integer from 3 to 100, $R_1$ and $R_2$ are independently selected from the group consisting of: alkoxy, hydroxyl, and halo.

(44) The chromatographic material of any of clauses 37 to 43, wherein the first reactive group comprises a member selected from the group consisting of vinyl groups and allyl groups.

(45) The chromatographic material of any of clauses 37 to 44, wherein the functional group comprises a member selected from the group consisting of an alkyl and an aryl.

(46) The chromatographic material of any of clauses 37 to 45, wherein the functional group comprises a C4-C30 alkyl.

(47) The chromatographic material of any of clauses 37 to 46, wherein the second reactive group comprises a member selected from the group consisting of a vinyl group, an allyl group and a thiol group.

(48) The chromatographic material of any of clauses 37 to 47, wherein the hydrophobic neutral compound comprises acetanilide.

As used herein, including in the claims, unless the context indicates otherwise, singular forms of the terms herein are to be construed as including the plural form and vice versa. For instance, unless the context indicates otherwise, a singular reference, such as "a" or "an" means "one or more".

Throughout the description and claims of this specification, the words "comprise", "including", "having" and "contain" and variations of the words, for example "comprising" and "comprises" etc, mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

The use of any and all examples, or exemplary language ("for instance", "such as", "for example", "e.g." and like language) provided herein, is intended merely to better illustrate the invention and does not indicate a limitation on the scope of the invention unless otherwise claimed. No language in the specification should be construed as indicating any non-claimed element as essential to the practice of the invention.

Any steps described in this specification may be performed in any order or simultaneously unless stated or the context requires otherwise.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

What is claimed is:

1. A method of separating a sample, the method comprising:
    flowing a mobile phase containing the sample, the sample comprising one or more aminoglycoside antibiotics, through a chromatographic column to chromatographically separate the one or more aminoglycoside antibiotics from each other or from one or more components of the sample, wherein the column is packed with a chromatographic material, the chromatographic material comprising:
    a silica substrate having a surface; and
    a polymeric layer covalently bound to the surface,
    the polymeric layer comprising polymer molecules, each polymer molecule being attached to the surface via multiple siloxane bonds and each polymer molecule being connected to one or more functionalizing compounds that each comprise a functional group, wherein the functional group comprises C14-C22 alkyl, each polymer molecule containing multiple first reactive groups, and each polymer molecule containing multiple silyl groups for forming the multiple siloxane bonds,
    wherein the multiple silyl groups are distributed along a length of each of the polymer molecules, and
    wherein the polymeric layer is formed by covalently attaching the polymer molecules to the surface of the substrate via the multiple silyl groups distributed along the length of each of said polymer molecules and reacting the first reactive groups of the attached polymer molecules with the one or more functionalizing compounds, wherein the one or more functionalizing compounds each comprise a second reactive group, wherein the second reactive group is reactive with the first reactive group, and
    wherein the pH of the mobile phase is 1 or less.

2. The method according to claim 1, wherein the functional group is C14-C22 straight chain alkyl.

3. The method according to claim 1, wherein the first reactive groups comprise olefinic groups.

4. The method according to claim 1, wherein the first reactive groups comprise a member selected from the group consisting of vinyl groups and allyl groups.

5. The method according to claim 1, wherein all of the first reactive groups are vinyl groups.

6. The method according to claim 1, wherein there is a substantially uniform distance between adjacent first reactive groups of the polymer.

7. The method according to claim 1, wherein the second reactive group comprises a member selected from the group consisting of an olefinic group and a thiol group.

8. The method according to claim 1, wherein the second reactive group comprises a member selected from the group consisting of a vinyl group and an allyl group.

9. The method according to claim 1, wherein the polymer molecule is based on a vinylsiloxane.

10. The method according to claim 9, wherein the vinylsiloxane polymer has a formula I:

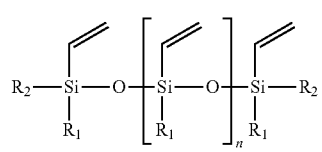

Formula I wherein n is an integer from 3 to 100, $R_1$ and $R_2$ are independently selected from the group consisting of: alkoxy, hydroxyl and halo.

11. The method according to claim 10, wherein $R_1$ and $R_2$ are independently selected from the group consisting of: methoxy, ethoxy and hydroxyl.

12. The method according to claim 10, wherein the vinylsiloxane polymer is a co-polymer.

13. The method of claim 1, wherein the one or more aminoglycoside antibiotics is selected from the group consisting of gentamicin, spectinomycin, kanamycin, ribostamycin, streptomycin, apramycin, paromomycin, dihydrostreptomycin, neomycin, netilmycin, tobramycin, amikacin, and arbekacin.

* * * * *